United States Patent
Seesselberg et al.

(10) Patent No.: US 11,147,447 B2
(45) Date of Patent: Oct. 19, 2021

(54) OPHTHALMIC SURGICAL MICROSCOPE

(71) Applicant: Carl Zeiss Meditec AG, Jena (DE)

(72) Inventors: Markus Seesselberg, Aalen (DE); Christoph Hauger, Aalen (DE); Artur Hoegele, Oberkochen (DE); Joachim Steffen, Westhausen (DE)

(73) Assignee: Carl Zeiss Meditec AG, Jena (DE)

( * ) Notice: Subject to any disclaimer, the term of this patent is extended or adjusted under 35 U.S.C. 154(b) by 229 days.

(21) Appl. No.: 16/526,971

(22) Filed: Jul. 30, 2019

(65) Prior Publication Data

US 2020/0029805 A1 Jan. 30, 2020

(30) Foreign Application Priority Data

Jul. 30, 2018 (DE) ..................... 10 2018 118 352.6

(51) Int. Cl.
*A61B 3/103* (2006.01)
*A61B 3/10* (2006.01)
*A61B 3/13* (2006.01)

(52) U.S. Cl.
CPC .............. *A61B 3/103* (2013.01); *A61B 3/102* (2013.01); *A61B 3/13* (2013.01)

(58) Field of Classification Search
CPC ............ A61B 3/103; A61B 3/102; A61B 3/13
USPC ........................................................ 351/221
See application file for complete search history.

(56) References Cited

U.S. PATENT DOCUMENTS

| | | | |
|---|---|---|---|
| 6,550,917 B1 | 4/2003 | Neal et al. | |
| 8,049,873 B2 | 11/2011 | Hauger et al. | |
| 9,615,740 B2 | 4/2017 | Hauger et al. | |
| 2008/0285043 A1 | 11/2008 | Fercher et al. | |
| 2014/0176904 A1 | 6/2014 | Lai | |
| 2015/0109580 A1 | 4/2015 | Hauger et al. | |
| 2015/0173609 A1 | 6/2015 | Seesselberg et al. | |

FOREIGN PATENT DOCUMENTS

| | | |
|---|---|---|
| DE | 102012012281 A1 | 12/2013 |
| DE | 102013021974 B3 | 3/2015 |
| EP | 1486160 A2 | 12/2004 |

(Continued)

OTHER PUBLICATIONS

Yifan Jian et al.: Wavefront sensorless adaptive optics optical coherence tomography for in vivo retinal imaging in mice, Biomedical Optics Express 2014, pp. 547-559.

*Primary Examiner* — Mohammed A Hasan
(74) *Attorney, Agent, or Firm* — Falk Ewers; Ewers IP Law PLLC

(57) ABSTRACT

An ophthalmic surgical microscope includes a main objective lens, through which an observation beam path passes, and a confocal optical system configured as a refractometer to determine the refraction of an eye. The optical system includes a measurement light source to generate a measurement light beam, a light detector to measure an intensity of measurement light and an optical unit to direct the measurement light beam onto the retina of the eye and to return measurement light reflected back at the retina to the light detector. The optical system includes an adaptive optical module (AOM) to modify a wavefront of the measurement beam path such that an intensity of the back-reflected measurement light changes. A spherical equivalent (SE) of the ametropia of the eye is determined based on a setting of the AOM, at which the measured intensity of the back-reflected measurement light has a maximum.

20 Claims, 20 Drawing Sheets

(56) References Cited

FOREIGN PATENT DOCUMENTS

| | | |
|---|---|---|
| JP | 07023908 A | 1/1999 |
| WO | 2007065670 A2 | 6/2007 |

OPHTHALMIC SURGICAL MICROSCOPE

CROSS REFERENCE TO RELATED APPLICATIONS

This application claims priority to German patent application DE 10 2018 118 352.6, filed Jul. 30, 2018, the entire content of which is incorporated herein by reference.

TECHNICAL FIELD

The disclosure relates to an ophthalmic surgical microscope having a main objective lens, through which an observation beam path passes, and including a confocal optical system, which is configured as a refractometer for determining the refraction of an eye of a patient.

BACKGROUND

An ophthalmic surgical microscope is known from US 2015/0109580 A1.

In the related art, appliances for determining the refraction of an eye of a patient are known, which can be used to simultaneously measure the spherical equivalent of the ametropia, the astigmatism, and the axis position of the astigmatism. These appliances include a wavefront sensor, for example a Hartmann-Shack sensor, a Talbot-Moiré sensor, or the like. Such refractometers may contain displaceable lens elements for reducing the curvature of the wavefront striking the wavefront sensor in such a way that it is also possible to measure eyes with pronounced ametropia.

Such a refractometer including a wavefront sensor is known from U.S. Pat. No. 6,550,917 B1. This refractometer includes displaceable optical components in order to reduce the curvature of the wavefront striking the wavefront sensor, depending on the ametropia of the patient's eye. Here, the variable lenses may also be used as adaptive optical elements, said variable lenses being able to be positioned in a conjugate plane to the surfaces of the eye.

The ophthalmic surgical microscope known from the aforementioned document US 2015/0109580 A1 has a confocal refractometer without a wavefront sensor; this is advantageous since wavefront sensors are sensitive to stray light, the latter arising on the cornea, the lens of the eye or lens surfaces, for example, and wavefront sensors moreover are expensive optical components.

However, a disadvantage of this known surgical microscope is that it only facilitates the measurement of the spherical equivalent of the ametropia, but not the measurement of the astigmatism and the axis position thereof. A quantitative determination of the astigmatism and its associated axis position is not possible using this known refractometer, even if the use of cylindrical lenses is specified. Consequently, this surgical microscope is not suitable, for example, for an intraoperative check of whether a toric intraocular lens inserted into the patient's eye is correctly oriented to compensate the astigmatism.

Document U.S. Pat. No. 8,049,873 B2 describes an ophthalmic surgical microscope, which includes an integrated refractometer and an optical coherence tomography (OCT) system. The refractometer is based on wavefront sensors, such as, e.g., a Hartmann-Shack sensor, with the aforementioned disadvantages. By pivoting-in a fundus imaging system below the main objective lens, it is possible to both image the retina and generate an OCT scan of the retina. The refractometer of this surgical microscope is not based on the confocal principle, and so the refractometer is sensitive to stray light which, for example, arises at the cornea and other interfaces in the patient's eye or which may also be caused by reflections at lens surfaces in the appliance itself.

U.S. Pat. No. 9,615,740 B2 describes a surgical microscope including a confocal measuring apparatus for determining the spherical equivalent and optionally including an OCT system. The refractometer of this surgical microscope allows measurement of the spherical equivalent of the ametropia; however, the astigmatism and the axis position of the astigmatism cannot be measured. Consequently, this surgical microscope is not suitable either for an intraoperative determination as to whether a toric intraocular lens inserted into the patient's eye is correctly oriented for compensating the astigmatism.

DE 10 2013 021 974 B3 describes an apparatus for determining the ametropia of an eye, including a measurement light source and a beam-shaping optical unit and an analysis module which includes a detector and an analysis optical unit. The analysis optical unit is configured to focus a parallel light beam, entering through the optical interface, along a predetermined and extended line that extends transversely to the direction of the analysis beam path. The detector is a spatially resolving detector, wherein an acute angle between a surface normal of the detection surface and the predetermined line is less than 80°. A controller is configured to obtain light intensity data detected by the detector and to establish ametropia data from the light intensity data, said ametropia data representing the ametropia of the eye. This apparatus likewise is not based on the confocal principle.

US 2014/0176904 A1 describes an ophthalmic aberrometer based on wavefront sensors, having the aforementioned disadvantages.

Furthermore, apparatuses for OCT are known; these can be used to undertake measurements on an eye of a patient, for example in order to measure and represent structures of the anterior chamber of the eye or of the retina of the eye in three dimensions. Usually, such an OCT apparatus includes an interferometer including a reference arm and a measuring arm, which reaches up to the region of the eye to be examined by the OCT light. Such an OCT apparatus is described in the article by Y. Jian, J. Xu, M. A. Gradowski, S. Bonora, R. J. Zawadzki, M. V. Sarunic: "Wavefront sensorless adaptive optics optical coherence tomography for in-vivo retinal imaging in mice", Biomedical Optics Express 2014, pages 547-559, DOI: 10.1364/BOE.5.00547. In this OCT apparatus, the fiber end of a light guide is imaged on the retina of a mammalian eye. The measurement light scattered by the retina shines through the optical unit a second time and is coupled into the fiber end, which simultaneously represents a confocal stop. The apparatus has an adaptive mirror available as an adaptive optical element, which can be used to compensate aberrations of the examined eye. Further, the article describes an algorithm of how the adaptive optical element can be actuated such that the measurement light coupled back into the fiber has an intensity that is as high as possible. However, this OCT apparatus is no refractometer but instead achieves the object of generating an OCT image of the retina with the highest possible quality. This is because, according to the article, the OCT image has particularly high quality if the light coupled back into the fiber has a high intensity. This known OCT apparatus is unsuitable for use as a refractometer, specifically for the following reasons: The adaptive mirror has a very small deflection of only 5 μm. This is clearly too little for compensating an astigmatism of the cornea and maximizing the signal that is coupled back into the fiber. In order nevertheless to maximize the signal level, a contact glass is placed onto the eye. Consequently, an astigmatism that may be present is compensated and a high-quality OCT image is generated. However, the contact glass prevents a measurement of the astigmatism which is caused by an asymmetry of the cornea, in particular. As a result of using a contact glass, the assumption should be made that the mean spherical refractive power of the cornea is also influenced. Consequently, it is not possible to measure the spherical equivalent of the ametropia by this arrangement either. The use of a contact glass represents a significant intervention and is uncomfortable for the patient, and so the use of a contact glass should be avoided when possible.

SUMMARY

It is an object of the disclosure to provide an ophthalmic surgical microscope including an integrated confocal refractometer to determine the refraction of an eye of a patient in such a way that an astigmatism and the axis position thereof can be determined on the patient's eye with little structural outlay.

The object is achieved by the ophthalmic surgical microscope as disclosed herein.

The ophthalmic surgical microscope according to an aspect of the disclosure is equipped with an integrated confocal refractometer for determining the refraction of an eye of a patient, allowing not only the measurement of the spherical equivalent of the ametropia but also the astigmatism and its axis position for the examined patient's eye. Consequently, the surgical microscope according to the aspect of disclosure facilitates, for example, an intraoperative check of whether a toric intraocular lens inserted into the patient's eye is correctly oriented to compensate the astigmatism.

The confocal refractometer of the surgical microscope according to an aspect of the disclosure requires no wavefront sensor, as result of which the confocal refractometer is insensitive to stray light and can also be generated at lower costs. Instead, the variables of spherical equivalent of the ametropia, astigmatism and axis position are measured by measuring or detecting a maximum intensity of the back-reflected measurement light by means of the light detector.

The terms used in the present disclosure are explained below. The spherical equivalent SE and the astigmatism C are typically specified in diopter (D). Typically, eyes with the spherical equivalent of SE<0 D are referred to as nearsighted or myopic, while eyes with SE>0 D are referred to as farsighted or hyperopic. Patient's eyes with SE≈0 D are referred to as emmetropic or as having spherically perfect vision. The astigmatism C describes the difference of the refractive powers of the eye in two mutually perpendicular principal meridians. The axis position φ describes the position of these principal meridians, represents an angle and is specified in the unit of degrees (°). The confocal refractometer of the surgical microscope according to an aspect of the disclosure allows the variables SE, C and φ to be measured in a simple and accurate fashion without a wavefront sensor.

The following convention is used in the description of the present disclosure: The stigmatism C is always positive and satisfies C>0 D. In the two principal meridians, the refractive error of the patient's eye is described by SE±(½) C. The axis position φ describes the position of that principal meridian with the refractive error of SE+(½) C. Other conventions for describing the refractive error may also be used; however, these can always be converted into the convention specified above.

Within the scope of the present disclosure, an optical system facilitating "point-to-point" imaging is understood to be "confocal". Here, within the scope of a refraction measurement by the surgical microscope, a pinhole illuminated by measurement light from the measurement light source can be imaged on the retina of the patient's eye as a measurement light beam such that a light spot is generated on the retina. To this end, the measurement light beam is focused on the retina by a focusing optical unit such that the light spot can be chosen to be as small as possible on the retina. Some of the measurement light incident in the region of the light spot is scattered back by the retina such that light energy emerges from the eye as back-reflected measurement light. A confocal stop can be positioned in a plane conjugate to the retina, said stop at least partly passing the measurement light reflected back from the eye, wherein the intensity of the back-reflected measurement light passed by the stop is measured by the measuring module with the light detector. Typically, the end of an optical fiber can be used instead of a physical pinhole as the light source-side confocal stop and as a light detector-side confocal stop.

The confocal refractometer of the surgical microscope according to an aspect of the disclosure includes an adaptive optical module including an adaptive component configured to compensate an astigmatism with any axis position in the wavefront of the measurement light by adjusting the adaptive component. Expressed differently, the adaptive component serves to compensate an astigmatism of the examined eye and its axis position. The adaptive optical module may include at least one movable optical element and/or at least one optical element, the optical properties of which, more particularly the cylindrical refractive power thereof, being variable. It is understood that the adaptive optical module may include a plurality of adaptive components and also that the optical unit of the refractometer may include a plurality of adaptive optical modules. The adaptive optical module of the confocal refractometer of the surgical microscope according to an aspect of the disclosure is adjustable to compensate the spherical equivalent of the ametropia of the eye in the wavefront of the measurement light. The adaptive component of the adaptive optical module is moreover configured to at least partly compensate by way of an adjustment an astigmatism with any axis position in the wavefront of the measurement light. It is understood that the adaptive component may also be configured to compensate the spherical equivalent of the ametropia of the eye and an astigmatism with any axis position, wherein the adaptive optical module may include only the adaptive component in this case.

The measuring module of the confocal refractometer of the surgical microscope according to an aspect of the disclosure is configured to determine the astigmatism of the eye and the axis position thereof from a setting of the adaptive component in which the measured intensity of the back-reflected measurement light has a maximum.

Advantageous configurations of the ophthalmic surgical microscope according to various aspects of the disclosure are described below.

It is advantageous if the adaptive component is adjustable into a neutral setting, in which the adaptive component has no astigmatic power or virtually no astigmatic power.

What is advantageous here is that an approximate measurement of the spherical equivalent can initially be performed in the neutral setting of the adaptive component when determining the refraction of the eye of the patient by the surgical microscope, without needing to remove the adaptive component from the measurement beam path and hence further reducing the constructive outlay. Subsequently, the astigmatism and its axis position can be measured by adjusting the adaptive component from the neutral setting.

Here, the astigmatic power of the adaptive component is typically continuously adjustable.

An advantageously simple configuration of the adaptive component can be realized by virtue of the adaptive component including two cylindrical lenses that are twistable in relation to one another, the one cylindrical lens of which has a positive cylindrical refractive power and the other cylindrical lens has a negative cylindrical refractive power, wherein the positive and the negative refractive power are equal in terms of absolute value.

Such an adaptive component, which is also referred to as a Stokes lens, is advantageous in that it can be set in a neutral setting, in which the adaptive component has no astigmatic power since the positive refractive power and negative refractive power of equal absolute value cancel one another, and then an astigmatic power that compensates the astigmatism of the patient's eye can be set by twisting the cylindrical lenses against one another from the neutral setting. Then, the axis position of the astigmatism can be compensated by further twisting of both lenses together.

According to another aspect of the disclosure, the adaptive component provides both an adjustable spherical refractive power to compensate the spherical equivalent of the ametropia and an adjustable astigmatic refractive power to compensate the astigmatism.

Such an adaptive component, which is able to compensate both the spherical equivalent and the astigmatism with any axis position, is advantageous in that the adaptive optical module overall can be constructed from fewer optical components and moreover in that it is also easily possible to determine the three parameters of spherical equivalent, astigmatism and axis position from the setting of the adaptive component.

An exemplary embodiment of such an adaptive component includes the adaptive component including two plates which each have a surface contour, wherein the two surface contours are complementary to one another, and wherein the plates are displaceable in translational fashion and/or twistable, together and/or relative to one another.

Such an optical component is also referred to as an Alvarez manipulator. A variable spherical refractive power can be generated by a displacement in a first direction perpendicular to the optical axis of the two plates relative to one another and a variable cylindrical refractive power can be generated in the case of a displacement in a second direction, which is perpendicular to the optical axis and also perpendicular to the first direction. Then, the two plates should be rotated together about the optical axis in order to vary the axis position.

Further examples of adaptive components with which both a spherical refractive power and an astigmatic refractive power are adjustable include liquid-filled membrane lenses, liquid lenses, etc., which can generate a spherical refractive power and an astigmatic refractive power with any axis position without a mechanical movement being necessary.

Furthermore, it is advantageous if the adaptive component is positioned in a plane that is conjugate to a pupil of the eye during use of the surgical microscope.

An advantage of this measure is that the measurement light beam has a round cross section in the region of the eye pupil, independently of the set astigmatism of the adaptive component. A further advantage is that the astigmatism of the patient's eye compensated by the adaptive component has a diopter number that is virtually independent of the compensation of the spherical equivalent, particularly when the adaptive optical module includes an adjustable afocal telescope for the purposes of compensating the spherical equivalent of the ametropia.

If the adaptive component is located in a plane conjugate to the plane of the pupil of the eye of the patient, this is tantamount to the adaptive component, more precisely a light beam emanating from the adaptive component, being focused on the pupil of the eye. When a surgical microscope is used to examine the eye of the patient, the pupil of the eye of the patient is usually close to the focal plane of the main objective lens of the surgical microscope. What emerges therefrom is that, in this configuration, the adaptive component is also positioned in a conjugate plane to the eye-side focal plane of the main objective lens.

According to an aspect of the confocal refractometer, the measurement light source and the light detector are connected to an optical fiber, the free end of which forms an emergence end for the measurement light beam and an entrance end for the back-reflected measurement light, wherein the emergence end and the entrance end are confocal.

It is possible to dispense with a measurement light source-side pinhole and a detector-side pinhole, as a result of which the design of the refractometer is further simplified by virtue of the confocal property being obtained by way of a single optical fiber end.

According to an aspect of the disclosure, in conjunction with the aforementioned measure, a zoomable collimator is arranged downstream in the measurement beam path.

The beam diameter of the measurement light beam on the eye can be varied. Although a variation in the beam diameter of the measurement light beam on the eye can also be realized by virtue of a stop with an adjustable aperture being arranged in the measurement beam path, this is disadvantageous in that measurement light is lost when the stop is constricted in order to reduce the beam diameter on the eye. By contrast, the aforementioned configuration ensures that such a loss of the light power is avoided; i.e., the measurement light reflected back from the retina can be coupled back into the optical fiber in optimal fashion such that a higher used signal can be measured at the light detector. The collimator is typically located in the vicinity of the adaptive component, upstream or downstream thereof.

According to an aspect of the disclosure, particularly in conjunction with the use of an optical fiber for emitting the measurement light beam and for receiving the back-reflected measurement light, the optical system includes a lock-in amplifier arranged in the measurement beam path, said lock-in amplifier more particularly including a chopper wheel.

The light path between optical fiber and eye is blocked with a high frequency and released again with the aid of the lock-in amplifier, more particularly with the aid of a quickly rotating chopper wheel. Then, a background signal possibly present can be eliminated from the modulation of the light detector signal, said background signal possibly arising, for example, if light of the measurement light source in the fiber coupler is directly output coupled in the direction of the light detector without passing through the measurement beam path.

According to a further aspect of the disclosure, a deflection element is arranged in the measurement beam path, said deflection element periodically deflecting the measurement light beam in such a way that the measurement light beam is periodically moved on the retina of the eye.

As a result of this measure, the influence of speckle effects or of inhomogeneities of the retina can be suppressed or at least reduced. The light spot on the retina is typically moved by small distances at a high speed. Consequently, it is possible to average over different signal levels, which arise on account of inhomogeneities of the retina or on account of a speckle effect. By way of example, the deflection element can be an angled plane plate located in the non-parallel beam path and can be made to rotate. Alternatively, it is possible to use other types of variable beam deflection, e.g., scanning mirrors as are used in OCT systems. Alternatively and likewise advantageously, a periodic deflection of the measurement light beam on the retina of the eye can be achieved by virtue of the emergence end of the aforementioned optical fiber being moved periodically in transverse fashion to the emission direction of the measurement light beam, wherein this movement may be very quick. By way of example, a piezo-actuator may generate the movement of the optical fiber end.

As an alternative or in addition to a lock-in amplifier for suppressing stray light, and hence for improving the signal-to-noise ratio at the light detector, use can be made of a linear polarization filter in combination with a λ/4 plate in the measurement beam path. So as not to reduce the component of the used light of the measurement light reflected back by the retina by the λ/4 plate, provision can be made of a second λ/4 plate, the latter being positioned in such a way that as many optical surfaces as possible are situated between the two λ/4 plates.

The adaptive optical module includes an afocal telescope in a further exemplary embodiment. In particular, the adaptive optical module may include an afocal telescope that is adjustable to compensate the spherical equivalent of the ametropia of the eye.

An afocal telescope for use in the optical unit of the refractometer of the surgical microscope can be embodied as a Keplerian system or as a Galilean system, wherein a Galilean system is more compact than a Keplerian system.

Consequently, in the exemplary embodiment described above, the adaptive optical module includes an adjustable telescope for compensating the spherical equivalent of the ametropia and an adaptive component for the compensation of the astigmatism and its axis position. However, as already described above, the compensation of the spherical equivalent of the ametropia can also be realized by the adaptive component itself, by virtue of the latter being able to generate an adjustable spherical refractive power.

In a further exemplary embodiment of the measurement described above, the optical unit includes a first optical arrangement, through which the measurement beam path passes, wherein the adaptive component is arranged in the vicinity of a measurement light source-side focal plane of the first optical arrangement.

The first optical arrangement may include one or more lenses or lens groups. By arranging the adaptive component near a measurement light source-side focal plane of the optical arrangement, a light beam emanating from the adaptive component can be imaged on the pupil of the eye of the patient. In turn, the latter is advantageous in that the astigmatism of the eye of the patient can be compensated independently of the compensation of the spherical equivalent of the ametropia, as a result of which it is easier to determine the astigmatism of the patient's eye on the basis of adjusting the adaptive component.

Furthermore, as seen from the measurement light source, a second optical arrangement which converts the measurement beam path into a parallel beam path can be disposed downstream of the first optical arrangement.

As a result of this measure, the measurement beam path is guided through the main objective lens of the surgical microscope. The observation beam path of the surgical microscope is usually parallel after passage through the main objective lens, as seen from the object plane. If the measurement light beam, as seen from the measurement light source, enters the main objective lens as a parallel beam path, the adaptive component can be imaged in the pupil plane, as described above.

Furthermore, the surgical microscope according to an aspect of the disclosure may include a separation mirror to separate the observation beam path from the measurement beam path.

As seen in the direction toward the eye of the patient, the separation of observation light and measurement light can be implemented upstream of (above) the main objective lens of the surgical microscope or downstream of (below) the main objective lens. In the main objective lens, the measurement light beam path and the observation light beam path can be superposed in coaxial fashion, or the two beam paths can be off-centered from one another.

The measurement beam path passes through the main objective lens in an exemplary embodiment. In this case, the separation mirror is located upstream of the main objective lens, as seen in the direction toward the eye of the patient.

According to an aspect of the disclosure, the separation mirror does not reduce the working distance between the surgical microscope and the eye, and so the surgeon experiences no restrictions during operation on the eye.

In a further exemplary embodiment, the measurement beam path passes through the main objective lens in off-centered fashion in relation to an optical axis of the main objective lens.

This can be achieved by an appropriate off-centered arrangement of the separation mirror in relation to the optical axis of the main objective lens. This allows one or more beam paths to completely pass through the separation mirror for the purposes of observing the patient's eye while other beam paths do not pass through the separation mirror, but instead run laterally past the latter, for the purposes of observing the patient's eye.

In a further exemplary embodiment, an illumination beam path for illuminating an observation area passes through a part of the optical unit of the refractometer.

This exemplary embodiment contributes further to the compactness of the surgical microscope by virtue of at least some of the optical elements, both for the refraction measurement and for illumination, being used together for the observation. By way of example, illumination light can be coupled into the measurement beam path of the refractometer by a splitter mirror.

This splitter mirror can be transmissive in the visual spectrum of light while it is reflective for the measurement light for the refraction measurement, which may lie in the non-visual spectrum. Likewise, a fixation light can be input coupled in the direction of the patient's eye by such a splitter mirror, said fixation light being able to be seen by the patient and so the patient can gaze in that direction predetermined by the fixation light. This can ensure the patient correctly aligning their eye during the refraction measurement.

The surgical microscope according to an aspect of the disclosure may include not only an integrated refractometer, as described above, in integrated fashion, but also an OCT system to examine the eye by optical coherence tomography. Here, the optical system is also designed for examining the eye by coherence tomography such that no additional optical elements, or only an insubstantial number of additional optical elements, are required for both functions (refraction measurement and OCT recording). Consequently, a compact surgical microscope can be provided overall, said surgical microscope facilitating a visual observation of the eye (including a camera recording), a measurement of the refraction of the eye and an examination of the eye by optical coherence tomography, i.e., a 3D data capture.

If the surgical microscope according to an aspect of the disclosure includes an OCT system in addition to the refractometer, the distance of the eye of the patient relative to the surgical microscope can be measured by an OCT scan of the anterior chamber. Then, firstly, the eye of the patient can be positioned relative to the surgical microscope in such a way that the eye is located in its intended position. Alternatively, the measured refraction of the eye can also be corrected by calculation in such a way that the offset of the patient's eye from its intended position is taken into account. This is important, in particular, in the case of large values for the spherical equivalent of the ametropia, as occurs when measuring aphakic eyes, i.e., lens-free eyes, for example.

According to a further aspect of the disclosure, the same light source is used as an OCT light source of the OCT system and as a measurement light source of the refractometer and/or if the same detector is used as an OCT detector of the OCT system and as a light detector of the refractometer.

These configurations are particularly advantageous within the meaning of a particularly compact structure of the surgical microscope for the two functions of OCT measurement and refraction measurement.

According to an aspect of the disclosure, within the meaning of the particularly compact structure of the surgical microscope, an OCT measurement beam path for recording an OCT scan passes through the same optical elements as the measurement beam path for a refraction measurement or the measurement beam path for the refraction measurement passes through the same optical elements as an OCT beam path for recording an OCT scan.

According to another aspect of the disclosure, only one light source and/or only one detector are required overall for the OCT measurement and the refraction measurement, and also all optical elements, or virtually all optical elements, of the optical unit of the optical system are used by the measurement beam path for the refraction measurement and by the OCT measurement beam path for recording an OCT scan.

The OCT system can record an OCT scan of the anterior chamber of the eye of the patient, or an OCT scan of the retina of the eye of the patient can be recorded. In the latter case, a fundus imaging system can be pivoted-in between the main objective lens and the eye of the patient in order to focus the OCT measurement light onto the retina. If the optical unit of the refractometer includes an adjustable telescope, as provided in one of the aforementioned exemplary embodiments, focusing of the OCT measurement light onto the retina may also be implemented by an appropriate adjustment of the telescope.

In a further exemplary embodiment of the surgical microscope including an integrated refractometer and OCT system, an optical element, for example a lens, may be provided, said optical element, for the purposes of switching between a refraction measurement and an OCT measurement, being introducible into the measurement beam path of the refraction measurement or into the OCT measurement beam path or being removable from the measurement beam path of the refraction measurement or from the OCT measurement beam path.

Typically, only one optical element, typically a lens, may be provided, said lens, for the purposes of switching between a refraction measurement and an OCT measurement, being introducible into the measurement beam path of the refraction measurement or into the OCT measurement beam path or being removable from the measurement beam path of the refraction measurement or from the OCT measurement beam path. In this case, the OCT measurement beam path and the refraction measurement beam path, apart from a single optical element, only pass through optical elements that are used together, as a result of which the compactness of the surgical microscope is optimized, with the functionality being increased at the same time.

The optical unit of the optical system may have a scanning mirror arrangement, as is conventional in OCT systems, for the purposes of deflecting the OCT measurement beam in two dimensions for a scan. However, the scanning mirrors may also remain in the optical unit for a refraction measurement, i.e., the measurement beam path for the refraction measurement also passes through the scanning mirror arrangement. Here, the scanning mirrors can be used to quickly move the measurement light beam for the refraction measurement on the retina of the eye of the patient, as was already explained above.

A further advantage of using the same optical unit for the refraction measurement and OCT measurement includes the adaptive component being able to be used to compensate the astigmatism of the eye during an OCT scan of the retina. Typically, this is achieved by virtue of the adaptive component being imaged on the patient pupil, even during the OCT scan of the retina. Here, the adaptive component is set in such a way that the astigmatism of the eye of the patient is compensated. Consequently, the quality of the OCT scan of the retina can be improved in the case of an astigmatic eye of the patient since more detailed information about the retina can be obtained by the OCT scan.

In conjunction with an aforementioned exemplary embodiment according to which the refractometer includes a zoomable collimator, the aperture of the OCT measurement beam, and hence its Rayleigh range in the object space, can be variable with the aid of the zoomable collimator when recording an OCT scan. The Rayleigh range is a measure for the optical depth of field. If the Rayleigh range is varied, this facilitates matching of the optical depth of field to the OCT scanning depth, which is predetermined by the spectral width of the OCT measurement light, for example.

Overall, what can be noted as an advantage of also using the optical unit for the refraction measurement for an OCT measurement is that the functionality of the OCT system and the quality of the OCT imaging can be influenced positively.

The aforementioned introducible lens may have a negative refractive power or a positive refractive power and may be arranged in such a way that its focal plane is located in the vicinity of the scanning mirror arrangement, typically between the two scanning mirrors, such that the adaptive component is imaged into the plane of the pupil of the eye during an OCT measurement. Here, a fundus imaging system with a reducing optical unit and an ophthalmoscope loupe can be arranged in the OCT beam path during an OCT measurement. The introducible lens has been removed from the measurement beam path during a refraction measurement, just like the optional fundus imaging system, and so the adaptive component can likewise be imaged into the pupil plane of the examined eye during a refraction measurement.

According to a further aspect of the invention, the refractometer includes a control unit for adjusting the adaptive optical module.

Here, the control unit, more particularly in conjunction with the measuring module of the refractometer, may be configured to adjust the adaptive optical module in such a way that the intensity of the back-reflected measurement light, as measured at the light detector, has a maximum.

The control unit can have a fully automated embodiment; in particular, provision can be made for feedback of the intensity of the back-reflected measurement light captured by the light detector to be provided at the control unit in such a way that the control unit adjusts the adaptive optical module until the intensity of the back-reflected measurement light measured at the light detector has a maximum.

The control unit can be configured to initially adjust the adaptive optical module during a neutral setting of the adaptive component, in which the adaptive component has no astigmatic power, until the intensity measured at the light detector has a maximum.

If a first and a second maximum is detected at the light detector on account of the astigmatism of the patient's eye present, the measuring module can determine the spherical equivalent from the respective setting of the adaptive optical module, and the astigmatism can be determined at least approximately from the two maxima.

Moreover, the measuring module can be configured to determine the spherical equivalent and determine the astigmatism as at least approximately 0 from the setting of the adaptive optical module when only one maximum is detected at the light detector.

Furthermore, the control unit can be configured to adjust the adaptive component from the neutral setting in such a way that the adaptive component compensates the astigmatism without consideration of the axis position thereof and can be configured to further adjust the adaptive component until the intensity detected at the light detector increases no more, wherein the measuring module is configured to determine the axis position of the astigmatism from the resultant setting of the adaptive component.

The aforementioned algorithms for determining the spherical equivalent of the ametropia, the astigmatism and its axis position can be stored as a computer program in the control unit and/or in the measuring module.

It goes without saying that the aforementioned features and the features yet to be explained below can be used not only in the respectively specified combination but also in other combinations or on their own, without departing from the scope of the present disclosure.

BRIEF DESCRIPTION OF THE DRAWINGS

The disclosure will now be described with reference to the drawings wherein.

DESCRIPTION OF EXEMPLARY EMBODIMENTS

Figure 1:
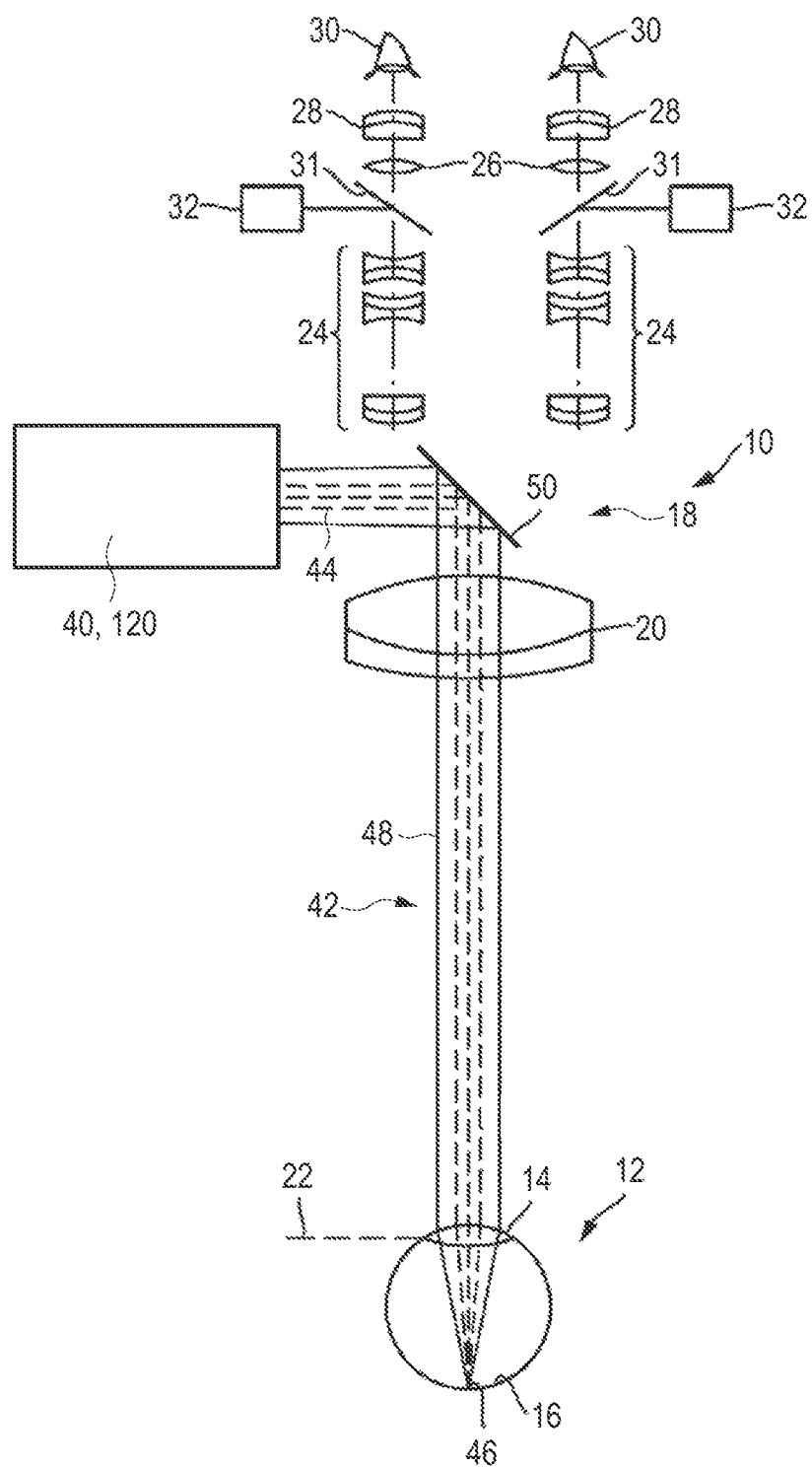
FIG. 1 shows a schematic illustration of an ophthalmic surgical microscope including an optical system, shown as a block, configured as a refractometer and, optionally, as an OCT system, wherein a beam path of the optical system passes through the main objective lens of the surgical microscope.

FIG. 1 shows an ophthalmic surgical microscope 10 for examining an eye 12 of a patient. The eye 12 includes a lens of the eye 14 and a retina 16.

The surgical microscope 10 provides an observation beam path 18 to observe or image sections of the eye 12. The microscope 10 includes a main objective lens 20, through which the observation beam path 18 passes. The section of the eye 12 to be imaged by the observation beam path is arranged in an object plane 22. Furthermore, the surgical microscope 10 includes a zoom system 24 for changing the magnification of the imaging. The observation beam path 18 passes through the zoom system 24 and a tube lens 26 and an eyepiece 28. The tube lens 26 and the eyepiece 28 generate an image of the object plane 22, which can be observed by a user of the surgical microscope 10 using their eye 30. Likewise, the object plane 22 can be imaged on a camera 32 via a beam splitter 31, said camera recording an image of the object plane.

In the exemplary embodiment shown in FIG. 1, the surgical microscope 10 has a pair of zoom systems, a pair of tube lenses, and a pair of eyepieces for producing stereoscopic images of the eye 12; however, this is purely exemplary and not mandatory for the present disclosure.

Furthermore, the surgical microscope 10 is equipped with a confocal optical system 40, which is configured as a confocal refractometer for determining the refraction of the eye 12 of the patient. In FIG. 1, the optical system 40 is shown schematically as a block. The refractometer 40 provides a measurement beam path 42 for the refraction measurement, said measurement beam path having a measurement light beam 44, which propagates from a measurement light source, yet to be described below, to the patient's eye 12 and which is focused on a small light spot 46 on the retina 16 of the eye 12, and measurement light 48 that is reflected back by the retina 16. The measurement light beam 44 and the back-reflected measurement light 48 are superposed on one another. The measurement light beam 44 and the back-reflected measurement light 48 should be understood to be beams of rays.

In the exemplary embodiment shown in FIG. 1, the measurement beam path 42 is concentrically superposed on the observation beam path 18 during the passage through the main objective lens 20, with this, however, not being mandatory. The measurement beam path 42 is separated from the observation beam path 18 by a separation mirror 50. In the exemplary embodiment shown in FIG. 1, the separation mirror 50 is located upstream of the main objective lens 20, as seen from the eyepiece 28, or above said main objective lens such that the measurement beam path 42 passes through the main objective lens 20.

Figure 2:
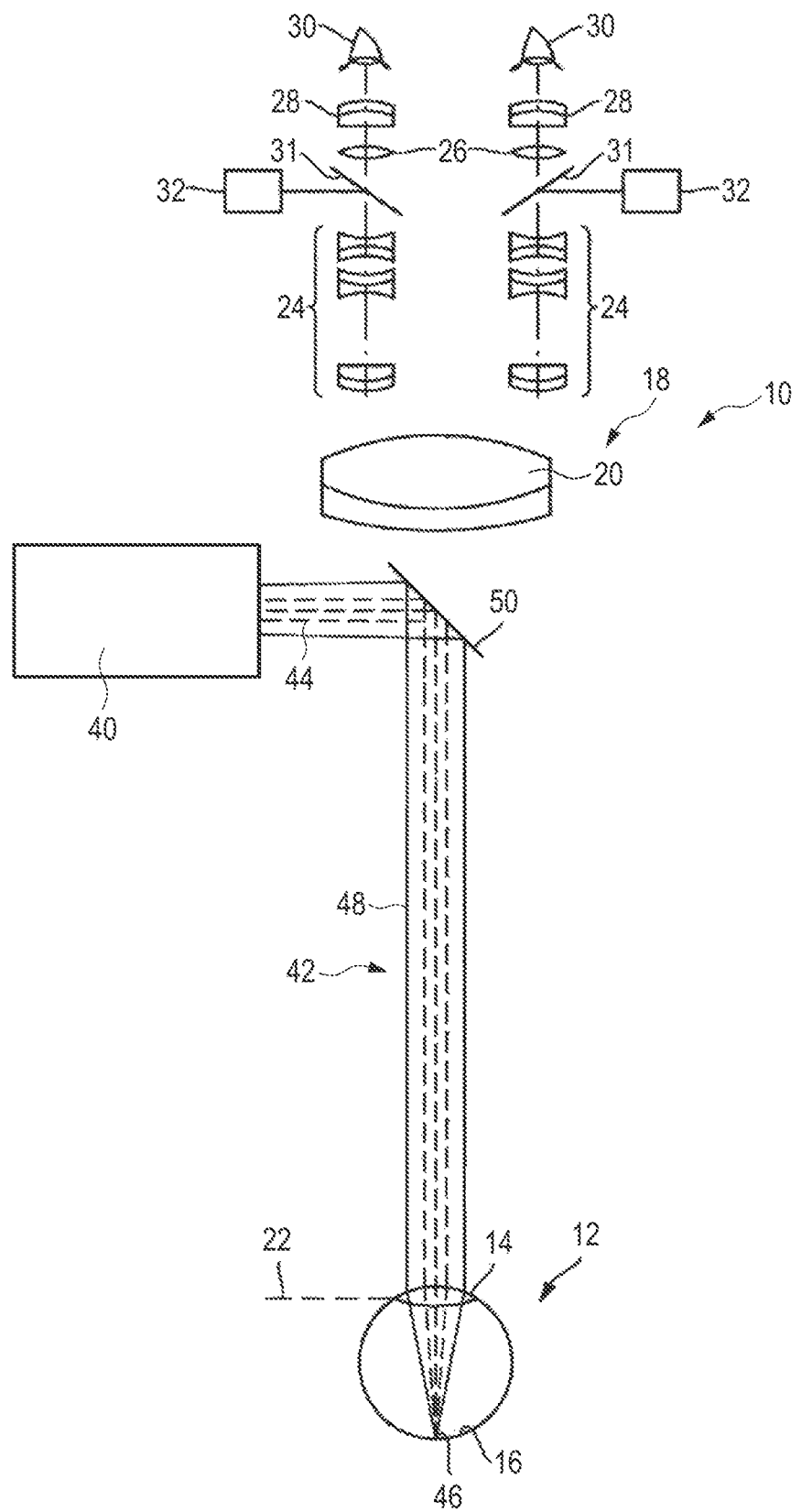
FIG. 2 shows a schematic illustration of an ophthalmic surgical microscope including an optical system, shown as a block, configured as a refractometer and, optionally, as an OCT system, wherein a beam path of the optical system passes through the main objective lens of the surgical microscope.

FIG. 2 shows an exemplary embodiment of the surgical microscope 10 that has been modified in relation to the exemplary embodiment shown in FIG. 1; here, the measurement beam path 42 for the refraction measurement does not pass through the main objective lens 20 of the surgical microscope 10. Accordingly, the separation mirror 50, as seen from the eyepieces 28 of the surgical microscope 10, is arranged downstream of the main objective lens 20 or below same.

By way of example, the separation mirror 50 in FIGS. 1 and 2 is configured to be transmissive for observation light in the visible spectrum and reflective for measurement light, which lies in the infrared spectral range, for example. The measurement light used by the refractometer 40 has a wavelength in a wavelength range around 1050 nm, for example.

Figure 3:
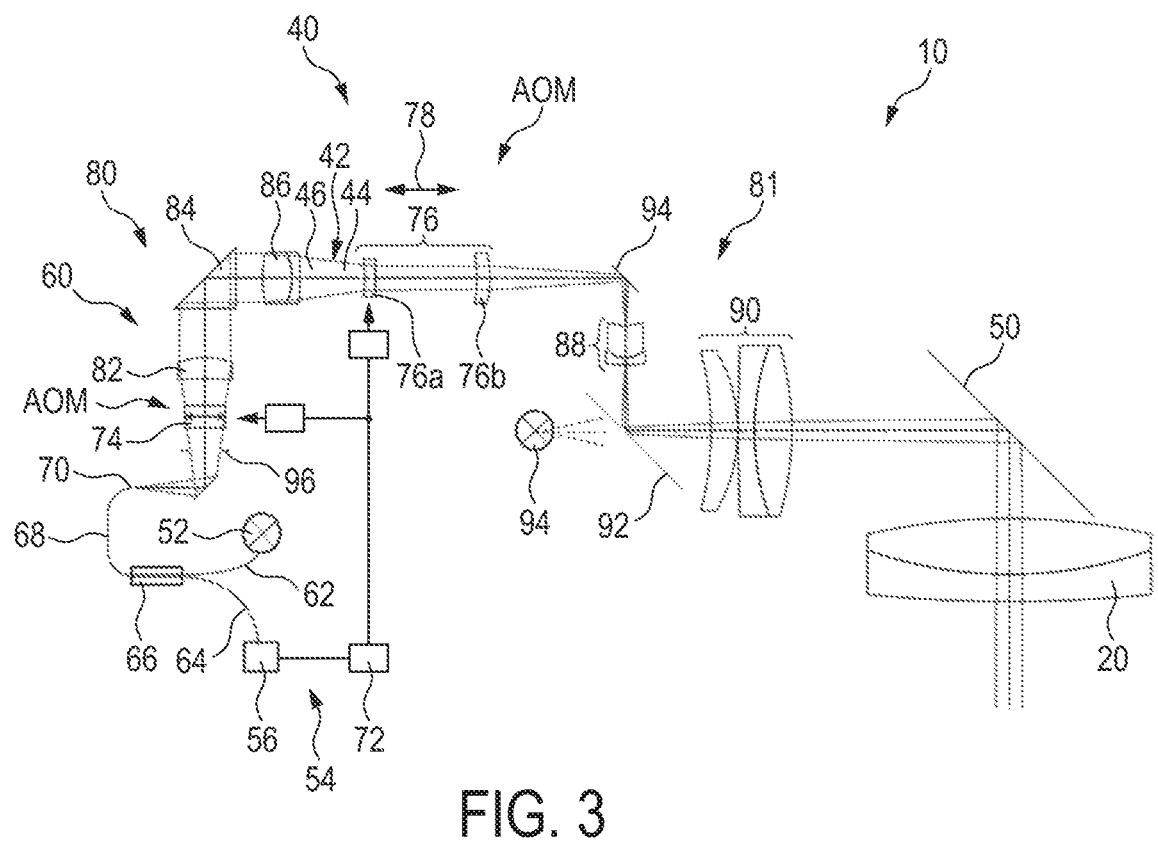
FIG. 3 shows an exemplary embodiment of the surgical microscope shown in FIG. 1 including an optical system for the refraction measurement, wherein only the main objective lens is shown from the remaining components of the surgical microscope.

With reference to FIG. 3, a first exemplary embodiment of the surgical microscope 10 is described in relation to the configuration of the refractometer 40. Of the remaining components of the surgical microscope 10 in FIG. 1, FIG. 3 merely shows the main objective lens 20 in order to provide a better overview. This also applies to the further exemplary embodiments yet to be described below.

In the exemplary embodiment shown in FIG. 3, the measurement beam path 42 passes through the main objective lens 20, as is shown for the surgical microscope 10 of FIG. 1.

The refractometer 40 includes a measurement light source 52 for emitting the measurement light beam 44. By way of example, a narrowband light source can be used as a measurement light source 52, said light source emitting light in the wavelength range around 1050 nm. However, a tunable light source, for example in the spectral range of 1050 nm±60 nm can also be used as a light source, as is conventional for OCT systems Furthermore, the refractometer 40 includes a measuring module 54, which includes a light detector 56 for measuring an intensity of back-reflected measurement light 48.

For the purposes of directing the measurement light beam 44 onto the retina 16 (FIG. 1) of the eye 12 (FIG. 1) and supplying measurement light 48 reflected back at the retina 16 to the light detector 56, the optical system 40 configured as a confocal refractometer here includes an optical unit 60 through which the measurement beam path 42 passes.

The measurement light source 52 is connected to a first optical fiber 62 and the light detector 56 is connected to a second optical fiber 64. The first optical fiber 62 and the second optical fiber 64 are connected to a third optical fiber 68 via a fiber coupling 66, or merge into said third optical fiber. A free end 70 of the third optical fiber 68 forms an emergence end for the measurement light beam 44 and an entry end for the back-reflected measurement light 48.

Overall, the measurement beam path 42 is confocal. In the optical system 40, "confocal" should be understood to mean that the measurement light beam 44 emerging from the free end 70 of the optical fiber 68 is imaged on the retina 16 in such a way that the small light spot 46 (FIG. 1) is generated on the retina 16 such that, overall, there is "point-to-point" imaging of the free end 70 of the optical fiber 68 on the light spot 46 on the retina 16 and that the measurement light 48 reflected back from the light spot 46 on the retina 16 is once again imaged on the free end 70 of the optical fiber 68. In so doing, the back-reflected measurement light 48 passes through the same optical elements as the measurement light beam 44.

The optical unit 60 of the refractometer 40 includes an adaptive optical module (AOM), which is adjustable in order to change a wavefront of the measurement beam path 42 in such a way that a spherical equivalent of the ametropia of the eye 12 and an astigmatism, including its axis position, can be compensated in the wavefront of the measurement light beam path. By adjusting the AOM, the components of which will still be described below, it is possible to vary the intensity of the back-reflected measurement light 48, which is measured or detected by the light detector 56, until a maximum intensity of the measurement light 48 reflected back by the retina 16 is measured. If the AOM is set such that the spherical equivalent of the ametropia and the astigmatism, including its axis position, are compensated, the intensity of the back-reflected measurement light 48 is maximal at the light detector 56. The measuring module 54 may include a control unit 72, which is connected, firstly, to the light detector 56 and, secondly, to the AOM to adjust the latter depending on the measured intensity until the intensity is maximal. The control unit 72 can use signals received from the light detector 56 for controlling the AOM.

In the exemplary embodiment shown in FIG. 3, the AOM includes an adaptive component 74 for compensating an astigmatism of the eye 12 of the patient, wherein the adaptive component 74 is configured to compensate astigmatism with any axis position. Furthermore, the AOM includes adjustable optical components for compensating the spherical equivalent of the ametropia of the eye 12 of the patient, wherein these components are formed by an adjustable afocal telescope 76 in the exemplary embodiment shown in FIG. 3. The afocal telescope 76 includes two lenses or lens groups 76a and 76b, which are displaceable, together and/or relative to one another, in the direction of the optical axis of the telescope 76 according to a double-headed arrow 78.

In the exemplary embodiment, the adaptive component 74 can be embodied as a Stokes lens, which has two cylindrical lenses that are twistable against one another about the optical axis, one lens of which has a positive cylindrical refractive power and the other has a negative cylindrical refractive power, wherein the positive and the negative refractive power are equal in terms of absolute value. Other possible realizations of the adaptive component 74 will still be described below.

In the exemplary embodiment shown in FIG. 3, the adaptive component 74 is arranged in the vicinity of the focus of the first optical arrangement 80, wherein the first optical arrangement includes a collimator 82, an optional half cube prism 84 and a lens group 86.

Typically, the adaptive component 74 is adjustable into a neutral setting, in which it has no astigmatic power or virtually no astigmatic power. In its neutral setting, the adaptive component 74 can generate aberrations which, in the case of a suitable configuration of the optical unit 60, only insubstantially impair the optical quality of the refraction measurement. Generally, such residual aberrations are smaller if the adaptive component 74 for compensating the astigmatism is located in the parallel beam path.

The telescope 76 of the AOM for compensating the spherical equivalent of the ametropia is an afocal optical system, in which light beams that are incident in parallel leave in parallel again, to a good approximation, after passing through the telescope 76. By way of example, the telescope 76 can be embodied as a Keplerian system or a Galilean system. A Galilean system is advantageous in that it is more compact than a Keplerian system. For the purposes of compensating the spherical equivalent of the ametropia, the telescope 76 can be displaced along its optical axis according to the double-headed arrow 78.

Furthermore, the optical unit 60 includes a second optical arrangement 81 including two lens groups 88 and 90 which, together, represent a further afocal telescope, which may be embodied as a Keplerian system or Galilean system, for example. Here, use is typically made of a Galilean system on account of the more compact embodiment of a Galilean system.

By way of example, the lens group 88 has a focal length of −10.7 mm and, for example, the lens group 90 has a focal length of 54 mm and the main objective lens 20 of the surgical microscope 10 has a focal length of 200 mm.

The optical unit 60 optionally includes a folding mirror 92, which is transmissive in the visual spectrum of the light such that light emitted by an illumination light source 94 can pass through the folding mirror 92 and can reach the patient's eye through the lens group 90 and the main objective lens 20. This renders it possible for the illumination beam path of the surgical microscope to pass through part of the optical unit 60 of the refractometer 40 for the purposes of illuminating an observation area that is observed with the surgical microscope 10 such that a compact structure of the surgical microscope 10 is facilitated for the illumination and refraction measurement functions.

Here, use can also be made of the so-called "red reflex illumination", as is used in eye examinations.

Likewise, a fixation light can be input coupled in the direction of the patient's eye by the folding mirror 92, said fixation light being able to be seen by the patient and so the patient can gaze in that direction predetermined by the fixation light. This ensures that the patient correctly aligns her/his eye during the refraction measurement.

The adaptive component 74 is arranged at a position or in a plane in the measurement beam path 42, said plane being conjugate to the plane of the pupil P of the patient's eye, which is located slightly in front of the lens of the eye 14. When examining an eye by an ophthalmic surgical microscope, it is typical for the pupil of the patient's eye 12 to be located near the object-side or eye-side focal plane of the main objective lens 20. If the adaptive component 74 is arranged near a conjugate plane to the pupil P of the patient's eye, this means, expressed differently, that a beam emanating from the adaptive component 74 is focused on the pupil P, as shown in FIGS. 4A to 4D. In particular, this property is satisfied independently of the position of the adjustable telescope 76 for compensating the spherical equivalent of the ametropia, as likewise shown in FIGS. 4A to 4D.

FIGS. 4A to 4D show three diagrams of beam paths of an optical system, configured as a refractometer, of the surgical microscope, wherein the optical system is constructed in similar fashion to the optical system of FIG. 3, wherein the three diagrams elucidate how an adaptive component for the compensation of an astigmatism is imaged into a pupil plane of the patient's eye, and a lower diagram showing a magnified section of the beam path.

It should be noted that the optical system 40 (refractometer) in FIGS. 4A to 4D differs from the system 40 in FIG. 3 by the lens group 88 being positioned upstream of the folding mirror 94 and by the optional folding mirror 92 not being present here. For reasons of simplification, in FIGS. 4A to 4D the same reference signs were used as in FIG. 3 for elements that are identical, similar or comparable to elements in FIG. 3.

Figure 4A:
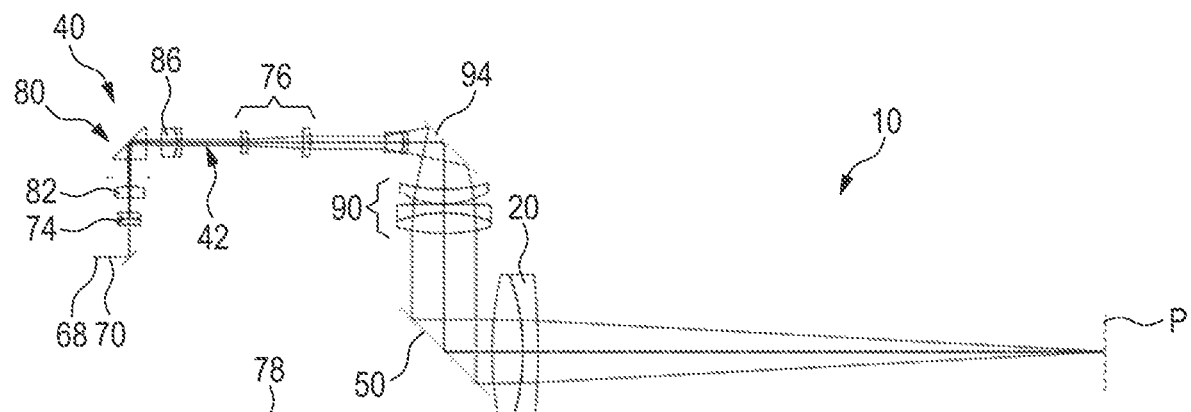
FIG. 4A shows a first diagram of beam paths of an optical system, configured as a refractometer, of the surgical microscope.
Figure 4B:
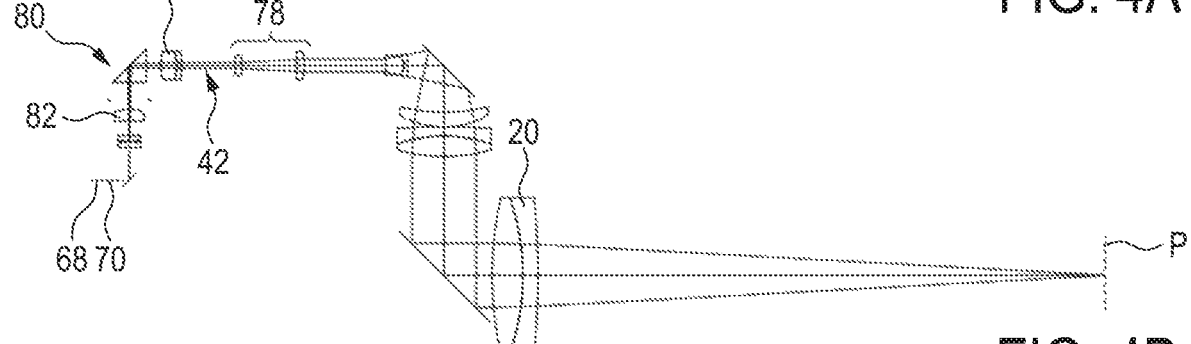
FIG. 4B shows a second diagram of beam paths of an optical system, configured as a refractometer, of the surgical microscope
Figure 4C:
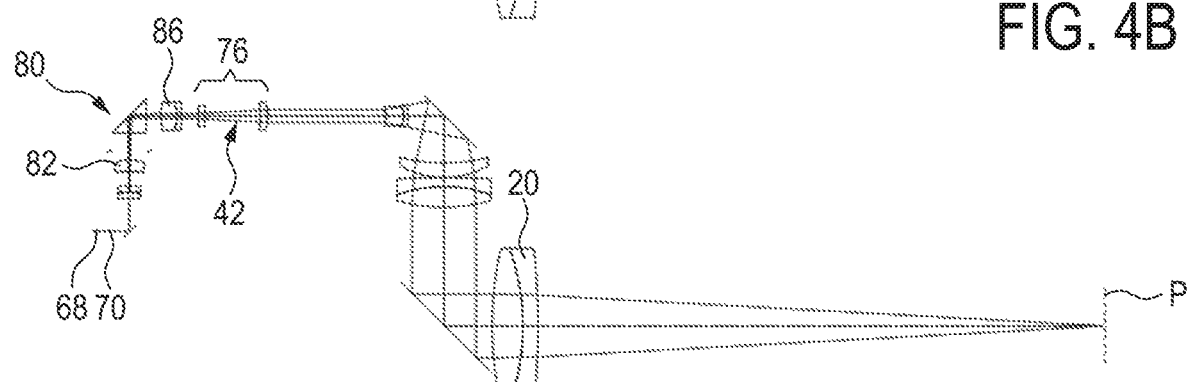
FIG. 4C shows a third diagram of beam paths of an optical system, configured as a refractometer, of the surgical microscope.

FIGS. 4A to 4C show the telescope 76 in three different displacement positions, and a point Z (FIG. 4D) is imaged on the pupil P independent of the respective displacement position. FIG. 4A shows the setting of the telescope 76 for compensating a spherical equivalent of a hyperopic eye, with a spherical equivalent SE=+20 D. FIG. 4B shows the setting of the telescope 76 for an emmetropic eye, i.e., an eye with perfect vision and SE=0 D. FIG. 4C shows a position of the telescope 76 for compensating a spherical equivalent of a myopic eye with a spherical equivalent SE=−15 D.

Figure 4D:
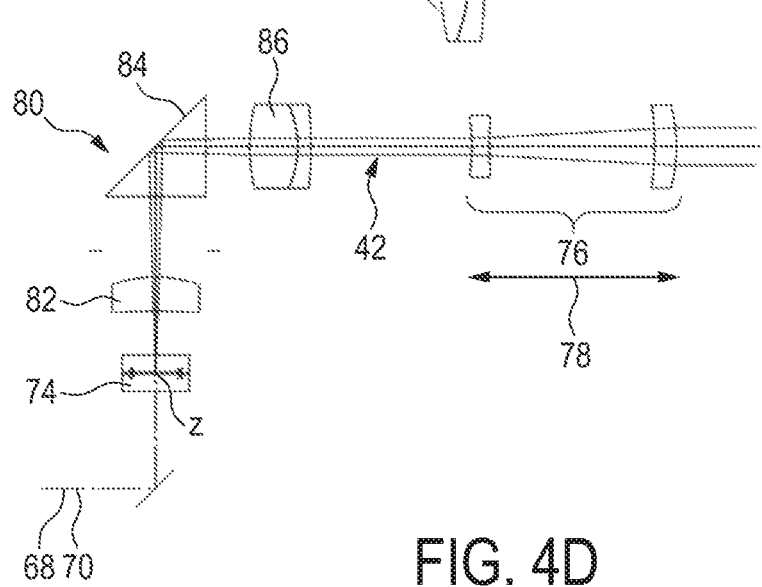
FIG. 4D shows a magnified section of FIG. 4B.
Figure 5A:
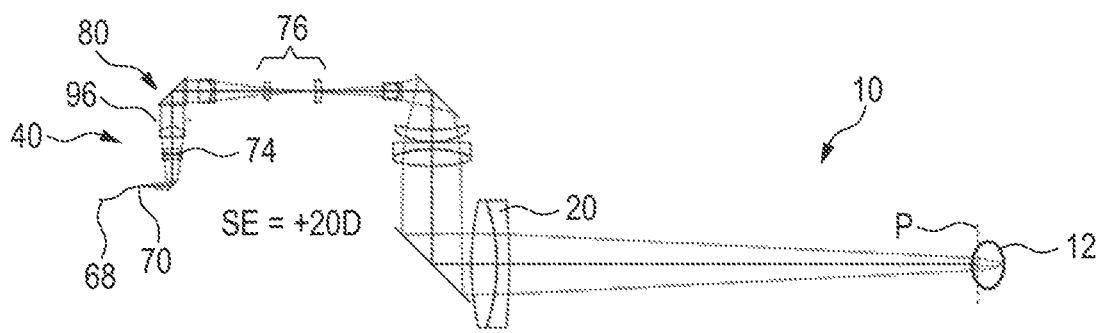
FIG. 5A shows a first diagram of measurement beam paths of the refractometer shown in FIGS. 4A to 4D for refraction measurements on patient's eyes with different spherical equivalents of the ametropia.
Figure 5B:
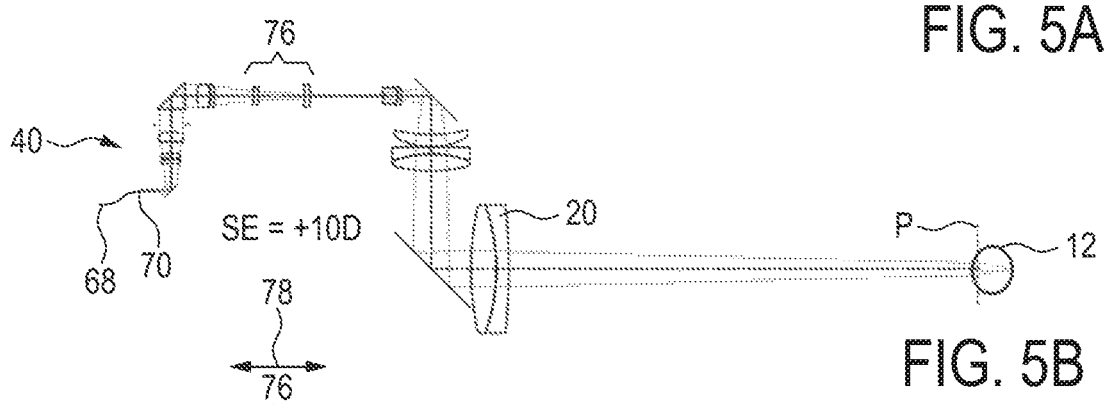
FIG. 5B shows a second diagram of measurement beam paths of the refractometer shown in FIGS. 4A to 4D for refraction measurements on patient's eyes with different spherical equivalents of the ametropia.
Figure 5C:
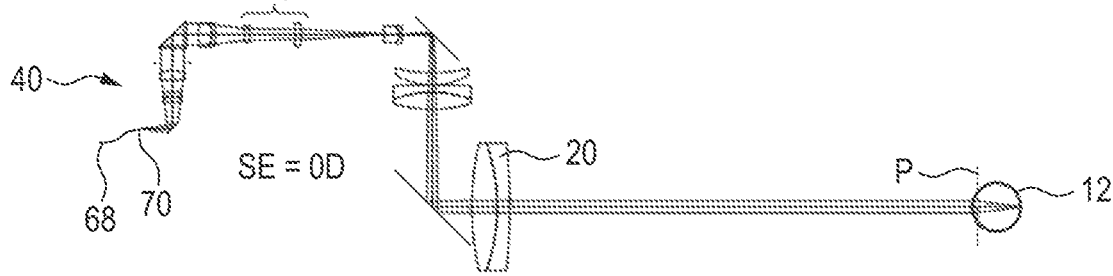
FIG. 5C shows a third diagram of measurement beam paths of the refractometer shown in FIGS. 4A to 4D for refraction measurements on patient's eyes with different spherical equivalents of the ametropia.
Figure 5D:
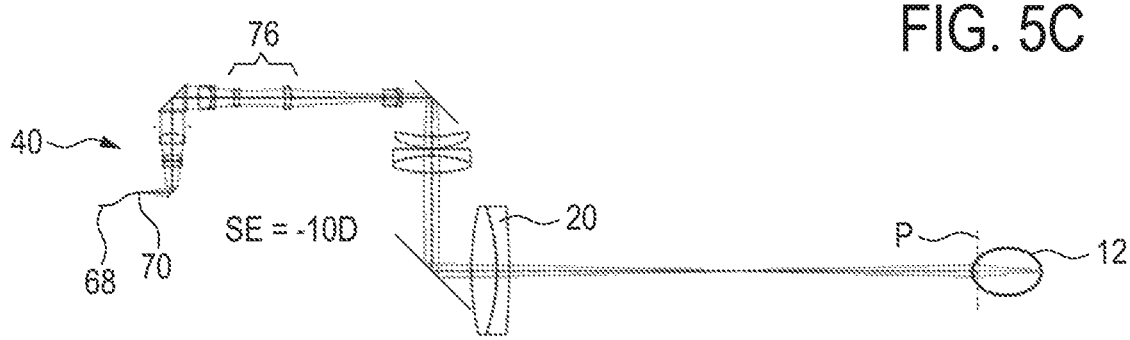
FIG. 5D shows a fourth diagram of measurement beam paths of the refractometer shown in FIGS. 4A to 4D for refraction measurements on patient's eyes with different spherical equivalents of the ametropia.
Figure 5E:
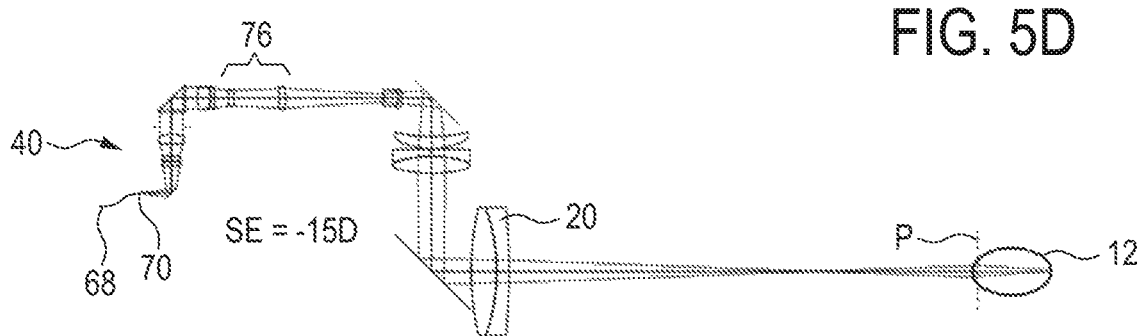
FIG. 5E shows a fifth diagram of measurement beam paths of the refractometer shown in FIGS. 4A to 4D for refraction measurements on patient's eyes with different spherical equivalents of the ametropia.

FIG. 4D shows a magnified section of FIG. 4B (SE=0 D) in the region of the measurement beam path 42 from the end 70 of the optical fiber 68 to the telescope 76 via the adaptive component 74.

If the point Z (FIG. 4D) in the center of the adaptive component 74 is considered, i.e., a point lying between the two cylindrical lenses on the optical axis in the case of a Stokes lens, and if imaginary light rays emanating from the point Z are considered, the latter are collimated after passing through the collimator 82 and the lens group 86 since the adaptive component 74, as described above, is located in the focal plane or at least in the vicinity of the focal plane of the optical arrangement 80 made of collimator 82, lens group 86 and the optionally provided half cube prism 84. Imagined light rays emanating from the point Z are parallel upstream and downstream of the afocal telescope 76, independent of the displacement position of the telescope 76 for compensating the spherical equivalent. Likewise, imagined light rays emanating from the point Z are parallel between the lens group 90 and the main objective lens 20 since the lens groups 88 and 90 once again represent an afocal telescope. Consequently, the imagined light rays emanating from the point Z are focused by the main objective lens 20 in the eye-side focal plane thereof. However, this is tantamount to the center Z of the adaptive component 74 for compensating the astigmatism being located in a plane conjugate to the eye-side focal plane of the main objective lens 20, in which the pupil P of the patient's eye 12 is typically located.

An advantage of positioning the adaptive component 74 in a plane conjugate to the pupil P of the patient's eye 12 is that the measurement light beam 44 has a round cross section in the region of the patient pupil P, to be precise, the measurement light beam 44 is independent of the setting of the adaptive component 74 for compensating the astigmatism of the patient's eye 12. A further advantage is that the astigmatism C of the patient's eye, compensated by the adaptive component 74, has a diopter number that is virtually independent of the position of the adjustable telescope 76 for compensating the spherical equivalent.

FIGS. 5A to 5E show the refractometer 40 of FIGS. 4A to 4D in the case of five refraction measurements on patients' eyes 12 with different spherical equivalents of the ametropia, with correspondingly five different settings of the telescope 76 for compensating a respective spherical equivalent from SE=+20 D to SE=−15 D. Since it is desirable also to be able to examine greatly hyperopic eyes using the surgical microscope 10, for example aphakic eyes, the refractometer 40 is particularly advantageous since it can compensate spherical equivalents in the range of −15 D<SE<+20 D.

It can also be seen from FIGS. 5A to 5E that the beam diameter of the measurement light beam at the eye 12 is independent of the displacement position of the telescope 76 for compensating the spherical equivalent. The reason for this lies in the fixed beam diameter at the adaptive component 74 for compensating the astigmatism and in the fact that the adaptive component 74 is located in a plane conjugate to the patient's pupil P. Consequently, the beam diameter on the eye 12 is constant even if the telescope 76 is displaced and approximately 5 mm in the shown example. In order to reduce the beam diameter of the eye 12, for example to diameter of 3 mm, a stop 96 can be arranged in the measurement beam path 42, the passage opening of said stop having a changeable cross section. The stop 96 can be arranged between the free end 70 of the optical fiber 68 and the adaptive component 74, as shown in FIG. 3, or within the optical arrangement 80 downstream of the adaptive component 74, as shown in FIGS. 4A to 4D and 5A to 5E. The beam diameter of the measurement light beam 44 of the eye 12 of the patient can be reduced or increased by constricting or opening up the stop 96.

Figure 6:
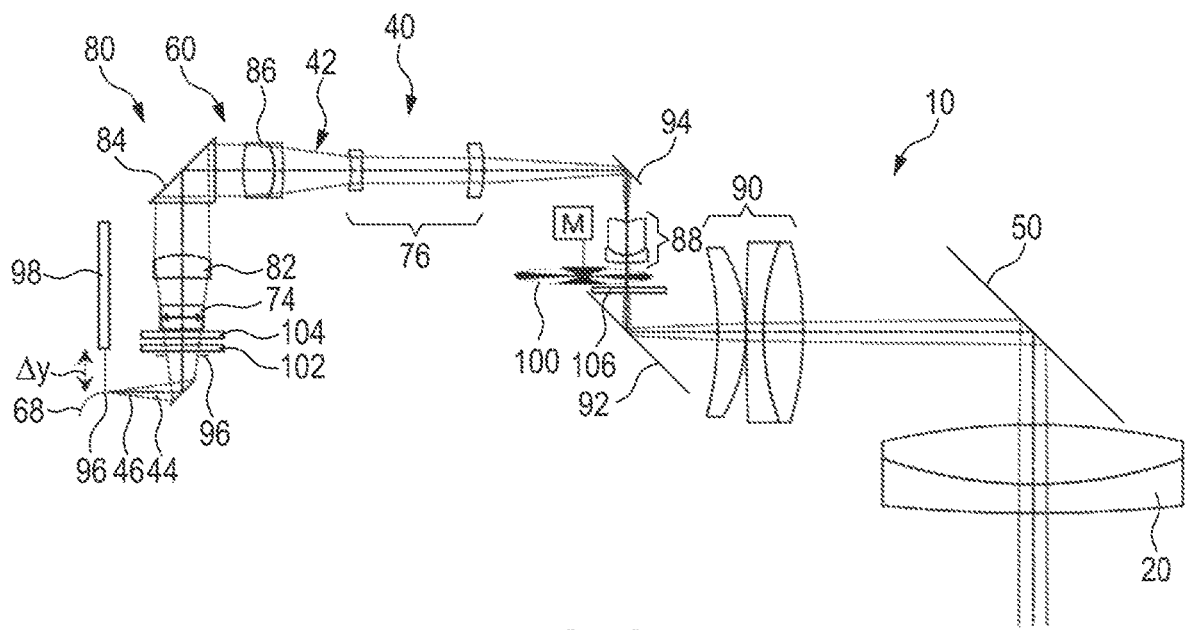
FIG. 6 shows an exemplary embodiment of the surgical microscope, modified in relation to FIG. 3, including an optical system, wherein only the main objective lens is shown from the remaining components of the surgical microscope.

FIG. 6 shows the refractometer 40 shown in FIG. 3 in a modification including further optional components. For reasons of simplification, in FIG. 6 the same reference signs were used as in FIG. 3 for elements that are identical, similar or comparable to elements in FIG. 3.

In the exemplary embodiment shown in FIG. 6, the end 70 of the optical fiber 68 is periodically movable back and forth in the direction perpendicular to the emission direction of the measurement light beam 44. By way of example, this can be realized by a piezo-actuator 98, which very quickly moves the end 70 of the optical fiber 68 back and forth through a distance Δy perpendicular to the light emission direction of the end 70 of the optical fiber 68. This leads to the light spot 46 (FIG. 1) on the retina 16 likewise moving quickly. By way of example, the distance Δy can be chosen in such a way that the light spot on the retina moves through a distance of Δ=10 μm or else Δ=50 μm.

A plane parallel plate (not shown) which has an inclination in relation to an optical axis and which is put into rotation may also be arranged in the non-parallel measurement beam path as an alternative to moving the end 70 of the optical fiber 68. By inclining the plane-parallel plate with respect to the optical axis, the measurement beam path 42 has a corresponding wobble-like movement.

An additional device in the refractometer 40 shown in FIG. 6 serves to suppress stray light that may cause problems during refraction measurement. However, it should be noted here that, on account of its confocal property, the refractometer 40 is already substantially less sensitive to stray light than refractometers with the wavefront sensors. In contrast to wavefront sensor-based systems, stray light sources, such as the corneal reflex, have no effect or at worst a small effect in the case of a confocal refractometer.

A possible source for disturbing stray light in the confocal refractometer 40 is that stray light that arises in the fiber coupling 66 (FIG. 3) and directly reaches the light detector 56 from the measurement light source 52, without having emerged from the end 70 of the fiber 68. This light reduces the signal-to-noise ratio. A further possible source of disturbing stray light are lens surfaces located in the vicinity of focuses of the measurement light beam path 42. In an exemplary embodiment, such a focus is located in the vicinity of the lens group 88 when the displaceable telescope 76 is near the position for an eye 12 with a spherical equivalent of SE=0 D. In order to take remedial action here, a lock-in amplifier with a chopper wheel 100 is provided in the refractometer 40 of FIG. 6, said chopper wheel being configured to be rotated by a motor M and serving to suppress stray light caused in the fiber coupling 66, for example, or stray light arising in the measurement beam path 42 between the end 70 of the optical fiber 68 and the chopper wheel 100. In the exemplary embodiment shown in FIG. 6, the chopper wheel 100 is located between the lens group 88 and the optionally provided splitter mirror 92 or, more generally, between the lens group 88 and the lens group 90.

The sensitivity to stray light can be reduced even further by virtue of combining a linear polarization filter 102 in combination with a first λ/4 plate 104. If polarized light emerges from the end 70 of the optical fiber 68, as is the case, for example, when using a superluminescent diode or a laser as a measurement light source 52, the linear polarization filter 102 and the first λ/4 plate 104 are rotated in such a way that the measurement light beam 44 can virtually entirely pass through the polarization filter 102 and is converted into circularly polarized light. Light reflected at the lens surfaces is virtually completely blocked by the linear polarization filter 102 on the return path in the direction of the end of 70 of the optical fiber 68. In order to avoid or at least reduce a loss of usable back-reflected measurement light 48, an optional second λ/4 plate 106 can be arranged in such a way that as many of the optical surfaces of the optical unit 60 as possible are located between the two plates 104 and 106. The second λ/4 plate 106 increases the reflected measurement light 48 coupled back into the optical fiber 68 and hence increases the measurement signal when the retina 16 scatters back polarized light in at least partly polarized fashion.

Figure 7:
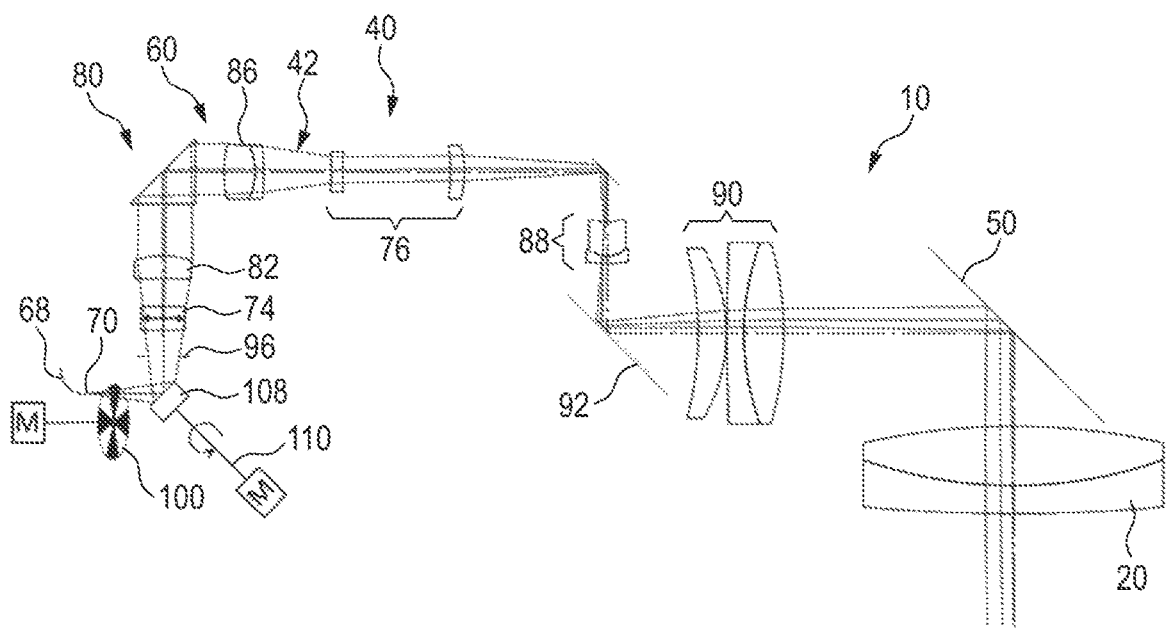
FIG. 7 shows a further exemplary embodiment of the surgical microscope, modified in relation to FIG. 3, including an optical system, wherein only the main objective lens is shown from the remaining components of the surgical microscope.

FIG. 7 shows a further exemplary embodiment of a surgical microscope 10 with an optical system 40 configured as a confocal refractometer, which is modified relative to the exemplary embodiments shown in FIG. 3 or FIG. 6 as follows: Here, the chopper wheel 100 for the lock-in amplifier is located in the vicinity of the end 70 of the optical fiber 68 and may have a compact structure since the beam cross section is small in this region. Furthermore, a deflection mirror 108 is arranged in the measurement light beam path 42, said deflection mirror being able to be put into rotation by a motor M in order to move the light spot 46 on the retina 16 (FIG. 1). The deflection mirror 108 includes a plate mirrored on one side with a slight wedge angle, a shaft 110 that is perpendicular to the back side of the plate being attached to the back side of said plate. The deflection mirror 108 is rotated about the shaft 110 by the motor M. Since the plate is wedged-shaped and not plane parallel, this leads to a deflection of the measurement beam path 42, which leads to a rotation of the light spot 46 on the retina 16. Depending on the property of the optical unit 60, the wedge angle of the plate now can be chosen in such a way that the light spot 46 on the retina 16 moves in a circle with a diameter of 10 μm or 50 μm, for example. FIG. 7 shows a corresponding measurement beam path 42 when the wedge angle of the plate is 0.5° and the shaft 110 is rotated in such a way that the normal vector of the mirrored side of the deflection mirror 108 lies in the plane of the drawing. It can be seen that the centroid ray of the beam now no longer extends along an optical axis of the optical unit 60.

The surgical microscopes 10 including the confocal refractometers 40 shown in FIGS. 3 to 7 can be used to measure the spherical equivalent SE, astigmatism C and the axis position φ of the astigmatism of the examined eye 12. The spherical equivalent SC is a statistic for the ametropia. Both the spherical equivalent SE and the astigmatism C are typically described in diopter (D). Usually, eyes with the spherical equivalent of SE<0 D are referred to as nearsighted or myopic, while eyes with SE>0 D are referred to as farsighted or hyperopic. Patient's eyes with SE≈0 D are referred to as emmetropic or having spherically perfect vision. The astigmatism C describes the difference of the refractive powers of the eye 12 in two mutually perpendicular principal meridians. The axis position φ describes the position of these principal meridians, represents an angle and is specified in the unit of degrees (°).

The following convention is used in the present description: The astigmatism C is always positive and satisfies C>0 D. In the two principal meridians, the refractive error of the patient's eye is described by SE±(½) C. The axis position φ describes the position of that principal meridian with a refractive error of SE+(½) C. It is understood that other conventions for describing the refractive error may also be used; however, these can always be converted into the conventions specified above. As described above, the adaptive component 74 may be embodied as a Stokes lens with two mutually twistable cylindrical lenses, one cylindrical lens of which has a positive refractive power $C_{zy1}$ and a second cylindrical lens has an equal magnitude, opposite negative refractive power $-C_{zy1}$. If one of the cylindrical lenses is rotated through an angle θ and the other is rotated through the angle -θ, the resultant cylindrical power is given by $C_{SL}=2\ C_{zy1}\cdot\sin(2\theta)$. Consequently, a Stokes lens allows generating a continuously adjustable cylindrical refractive power $C_{SL}$. It is possible to vary the axis position φ if both cylindrical lenses are rotated together. Other exemplary embodiments of the adaptive component 74 are likewise conceivable and will still be described below.

For the purposes of determining or measuring the refraction of the eye 12, i.e., for determining the values SE, C, and φ, the adaptive component 74 and the adjustable telescope 76 are set in such a way that the intensity of the back-reflected measurement light 48 at the light detector 56 is maximal. Then, the values SE, C, and φ can be determined from the associated settings of the adaptive component 74 and of the telescope 76.

Here, the method may be in steps. Initially, the adaptive component 74 can be set in its neutral setting, in which it develops no astigmatic power. Consequently, the astigmatism C generated by the adaptive component 74 is 0 D. The telescope 76 is displaced, typically by the control unit 72, in this position of the adaptive component 74 until a maximum intensity of the back-reflected measurement light is measured at the light detector 56. Here, feedback from the light detector 76 to the actuation unit 72 is used to prompt the control unit 72 to adjust the telescope 76 on the basis of the intensity signal at the light detector 56 until the measured intensity is at a maximum. The telescope 76 can also be displaced over its entire travel and an intensity curve can be recorded as a function of the position of the telescope 76.

If only one maximum of the intensity curve is present at the light detector 56, the value SE is estimated from the intensity curve depending on the position of the telescope 76 and the value C is set to a small value. If two intensity maxima are present in the intensity curve measured by the light detector 56, SE and C are estimated from the intensity curve on the basis of the associated positions of the telescope 76.

Next, the adaptive component 74 and the telescope 76 are set such that the estimated values for SE and C are compensated. Subsequently, the axis position of the adaptive component 74 is varied and the intensity at the light detector 56 is measured in the process. If the intensity depends on the axis position of the adaptive component 74, the axis position φ is determined as the one where the intensity is maximal. Subsequently, the adaptive optical module, i.e., the adaptive component 74 and the telescope 76, are set such that SE, C, and φ are compensated. Subsequently, attempts can optionally be made to further increase the intensity measured at the light detector 56 by varying the settings of the adaptive component 74 and of the telescope 76 until this is no longer possible. Then, the parameters SE, C, and φ that characterize the eye are determined from the settings of the adaptive component 74 and of the telescope 76. The known optical parameters, such as lens spacings, imaging scale of the telescope 76 and cylindrical refractive power of the adaptive component 74, are used to determine SE and C.

Referring back to FIG. 1, a configuration level of the surgical microscope 10 is described below, in which the confocal optical system 40/120 integrated into the surgical microscope 10 is configured not only as a refractometer 40 but also as an OCT system 120. What is highlighted here is that only a minimum of additional optical elements are required in the optical system for the purposes of integrating the combination of the two functions of refraction measurement and OCT-scan recording into the surgical microscope.

This is initially described on the basis of a further exemplary embodiment of a surgical microscope 10, which is shown in FIGS. 8A to 10E. For reasons of simplification, in FIGS. 8A to 10E the same reference signs are used as in FIGS. 1 to 7 for elements that are identical, similar or comparable to elements in FIGS. 1 to 7.

Figures 8A, 8B:
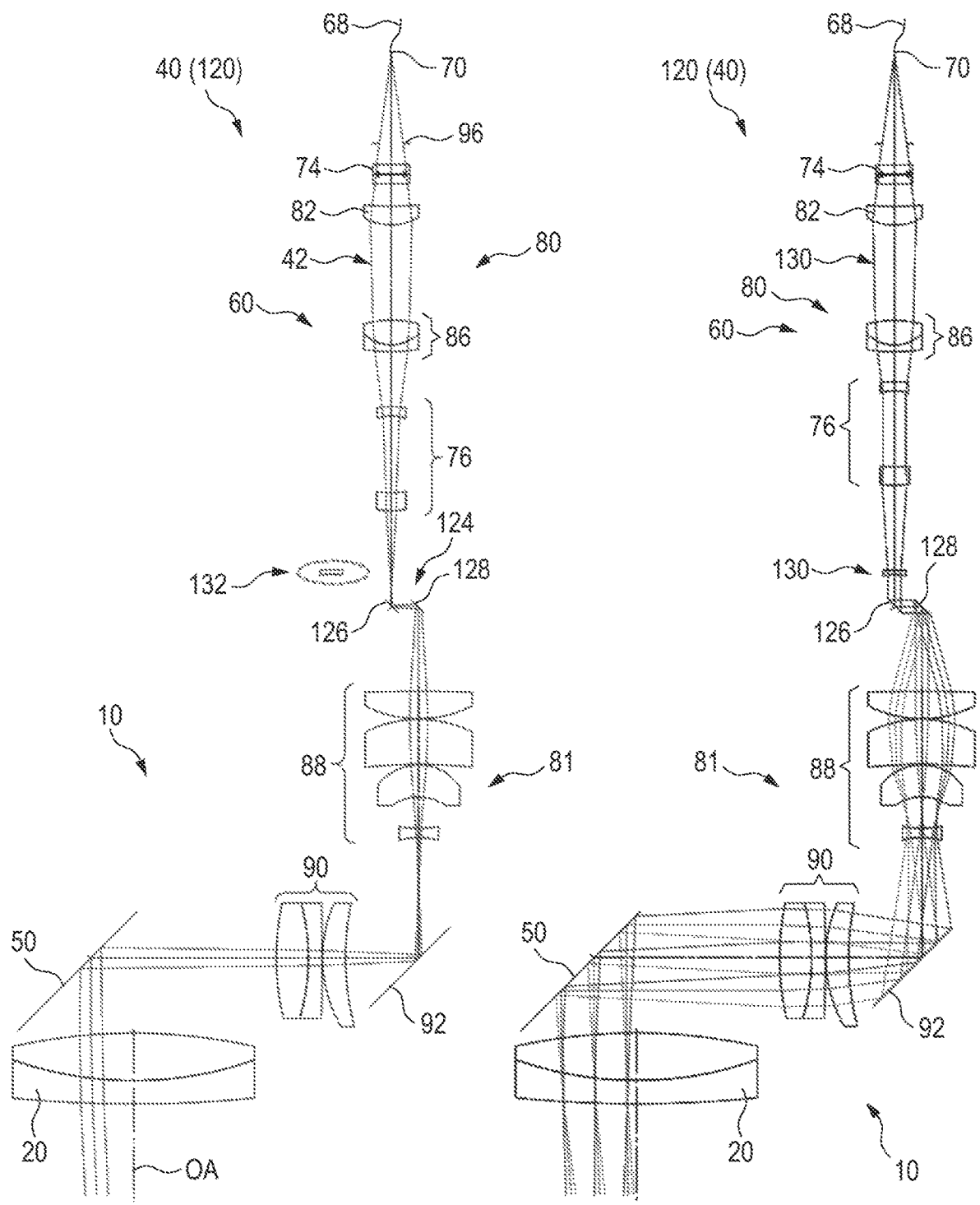
FIG. 8A shows a measurement beam path for a refraction measurement according to a further exemplary embodiment of the surgical microscope.
FIG. 8B shows an OCT beam path for recording an OCT scan according to the further exemplary embodiment of the surgical microscope.

Like in the preceding exemplary embodiments, the optical system 40/120 shown in FIGS. 8A and 8B is integrated into the surgical microscope 10 of FIG. 1, of which only the main objective lens 20 has been shown in addition to the optical system 40/120. Apart from minor modifications, the optical system 40/120 can be used as refractometer or as OCT system 120 in the surgical microscope 10, with the minor modifications still being described below.

The optical unit 60 of the optical system 40/120 includes the adaptive component 74, the first optical arrangement 80 including the collimator 82 and the lens group 86, the adjustable telescope 76, the second optical arrangement 81 including the lens groups 88 and 90, and the splitter or folding mirror 92. In comparison with the exemplary embodiment shown in FIG. 3, the optical unit 60 of FIGS. 8A and 8B does not include a half cube prism 84 and the lens group 88 has four lenses instead of two in this case.

Once again, the telescope 76 is embodied as an afocal adjustable telescope, which may be embodied as a Galilean system or a Keplerian system.

A scanning mirror arrangement 124 is arranged in the measurement beam path 42 between the telescope 76 and the second optical arrangement 81, more precisely the lens group 88. The scanning mirror arrangement 124 includes two scanning mirrors 126 and 128. The measurement beam path 42 also passes through the scanning mirror arrangement 124 in the case of a refraction measurement. Here, the scanning mirrors 126 and 128 are both drawn in the plane of the drawing; however, this only serves for simplification purposes. In fact, one of the two scanning mirrors 126 or 128 is rotated out of the plane of the drawing through 90° in order to be able to carry out a two-dimensional scan using the two scanning mirrors, as is conventional within the scope of an examination of the eye 12 by optical coherence tomography.

FIGS. 8A and 8B show a further exemplary embodiment of an ophthalmic surgical microscope including an optical system, which is configured for refraction measurement and for recording an OCT scan, in two partial images which show different modes of operation of the optical system, wherein FIG. 8A shows a measurement beam path for the refraction measurement and FIG. 8B shows an OCT beam path for recording an OCT scan, and wherein only the main objective lens is shown from the remaining components of the surgical microscope.

In the exemplary embodiment shown in FIGS. 8A and 8B, the second optical arrangement 81 is embodied, once again, as an afocal telescope, albeit as a Keplerian telescope in this case. Compared to the Galilean telescope, a Keplerian telescope has the property that a point between the scanning mirrors 126 and 128 can be imaged in the vicinity of the separation mirror 50 such that the separation mirror 50 can have a compact embodiment.

The optical system 40/120 includes the measurement light source 52 and the light detector 56 according to FIG. 3; however, these are not shown in FIGS. 8A and 8B.

The entire optical unit 60, the measurement light source 52, and the light detector 56 of the optical system 40/120 are used both during the refraction measurement and when recording OCT scans; i.e., an OCT beam path 130 passes through the entire optical unit 60 of the refractometer 40.

For the basic description of the functionality of an OCT system integrated in a surgical microscope, reference is made in exemplary fashion to document U.S. Pat. No. 8,049,873 B2, and therefore, a description thereof is dispensed with here.

In FIGS. 8A and 8B, the reference sign 120 has been placed in parentheses in FIG. 8A since the system 40/120 is used as a refractometer 40 in FIG. 8A. By contrast, in FIG. 8B, the system 40/120 is used as an OCT system 120, and therefore, the reference sign 40 is placed in parentheses in FIG. 8B. This is also maintained in the further figures.

FIG. 8A shows the optical unit 60, as traversed by a measurement beam path 42 for a refraction measurement of the patient's eye. FIG. 8B shows the optical unit 60, as traversed by an OCT beam path 130 for recording an OCT scan of the patient's eye 12. The optical unit 60 includes an additional optical element 132, which is embodied as a lens, more particularly as a negative lens, in the present case. The additional optical element 132 is introduced into the OCT beam path 130 for recording of an OCT scan, while it is removed from the measurement beam path 42 for a refraction measurement. By way of example, the optical element 132 can be pivoted in or out by a pivoting mechanism (not shown) or can be introduced and removed by a carriage.

In FIG. 8B, the OCT beam path 130 is shown from the scanning mirror 128 according to three different scanning mirror positions of the scanning mirror 128.

Figure 9A:
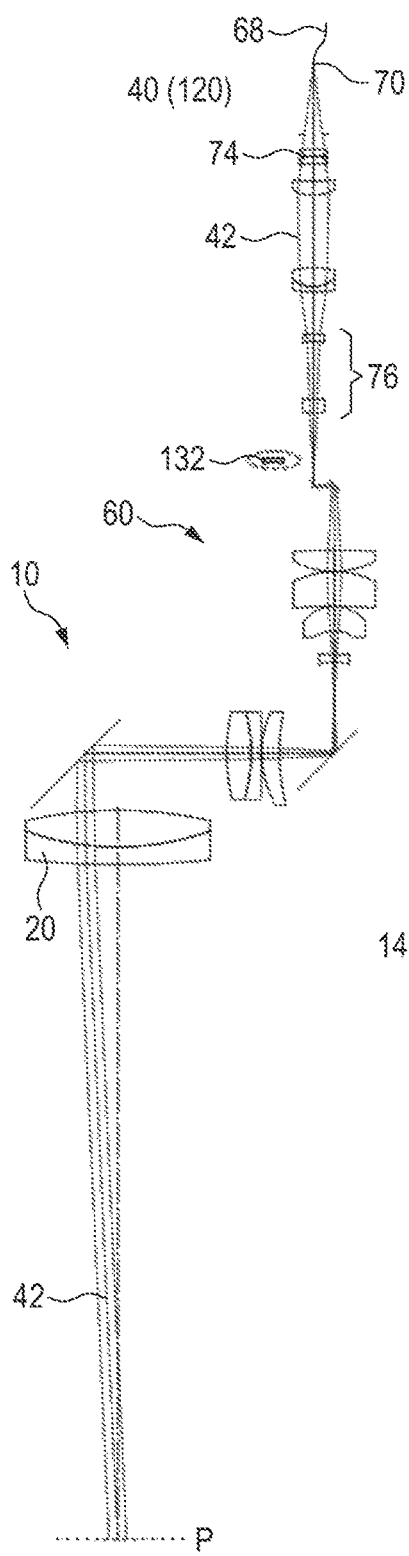
FIG. 9A shows a measurement beam path through the optical system for the refraction measurement.

Like in the previous exemplary embodiments, the adaptive component 74 for compensating the astigmatism is located near the focal plane of the optical arrangement 80 made of collimator 82 and lens group 86 and it is thus imaged on the pupil P of the eye 12 of the patient by the adjustable telescope 76 for compensating the spherical equivalent of the ametropia, the second optical arrangement 81, which includes the lens groups 88 and 90 in the form of an afocal telescope, and the main objective lens 20 when the optical element 132 has been removed from the measurement beam path 42, as shown in FIG. 9A, to be precise independently of the displacement position of the telescope 76.

As shown in FIGS. 8A and 8B, an optical axis OA of the main objective lens 20 is off-centered in relation to an optical axis between the end 70 of the optical fiber 68 and the lens group 90 by virtue of the separation mirror 50 having a suitable arrangement. This allows one or more beam paths to completely pass through the separation mirror 50 for the purposes of observing the patient's eye 12 by visible light, while other beam paths do not pass through the separation mirror 50, but instead run laterally past the latter, for the purposes of observing the patient's eye 12.

The measurement light source 52 of the refractometer 40 is also used as OCT light source of the OCT system 120 and the light detector 56 of the refractometer 40 is likewise used as OCT detector of the OCT system 120 such that only one light source and one detector are required for the two functions of refraction measurement and recording of OCT scans.

Figure 9B:
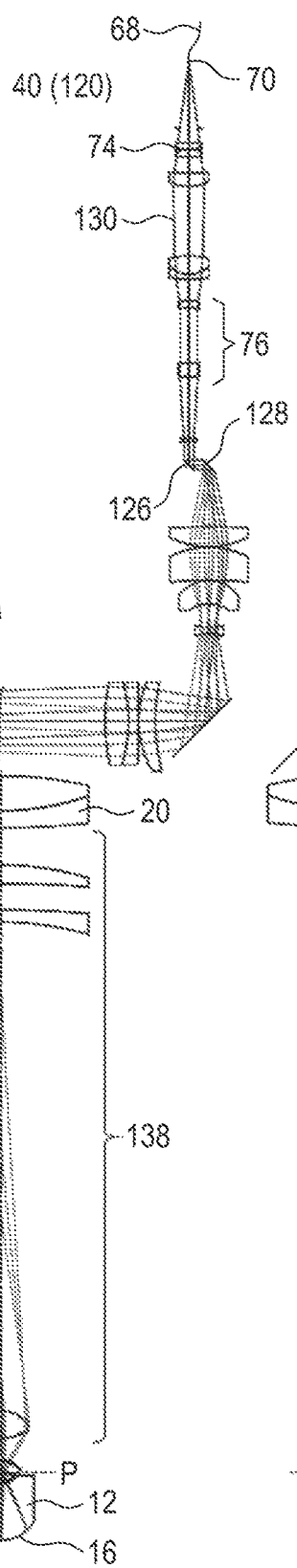
FIG. 9B shows an OCT path through the optical system for recording an OCT scan of the retina.
Figure 9C:
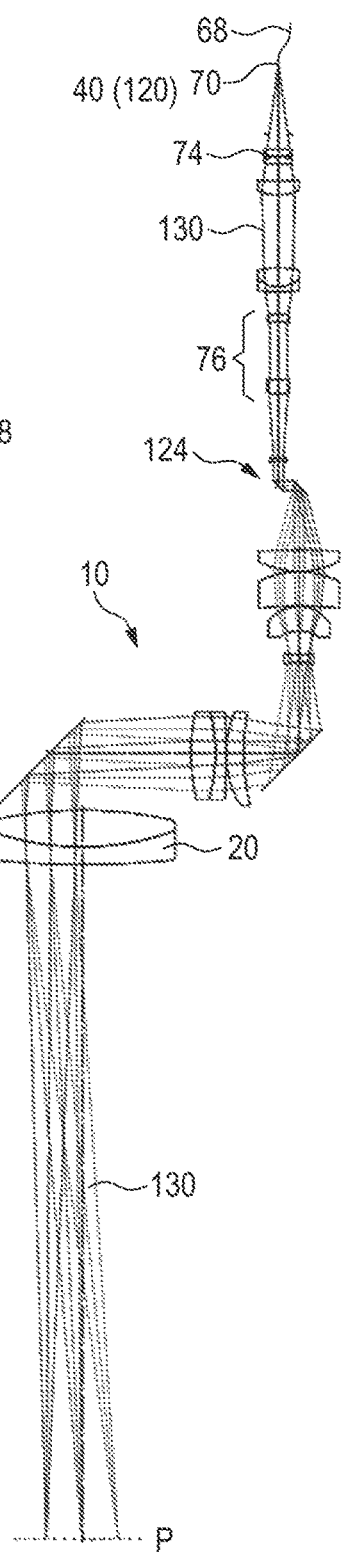
FIG. 9C shows an OCT beam path through the optical system for recording an OCT scan of the anterior chamber of the eye of the patient.
Figure 10A:
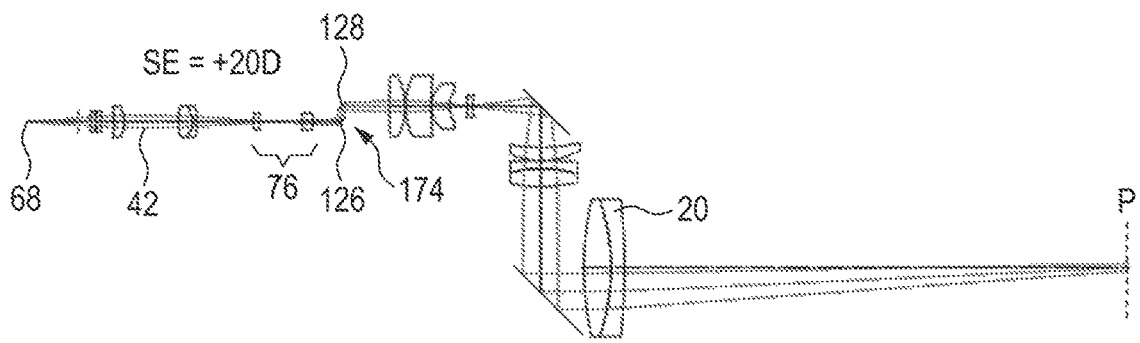
FIG. 10A shows a first diagram of measurement beam paths for the refraction measurement using the optical system shown in FIGS. 8A and 8B for patients' eyes with different spherical equivalents of the ametropia.
Figure 10B:
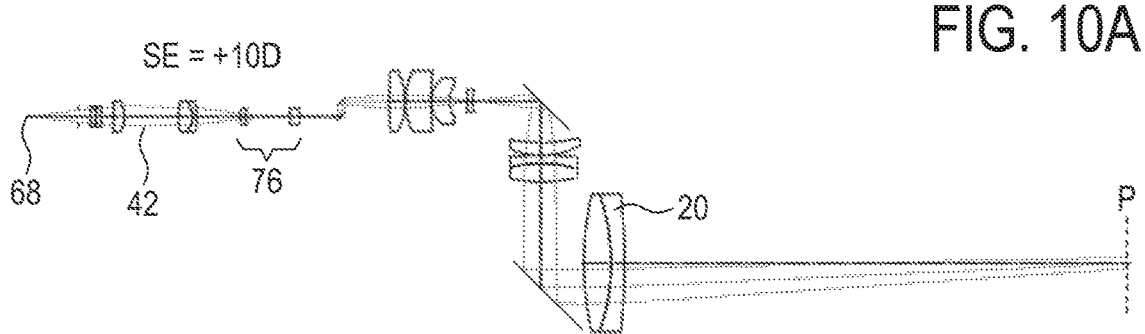
FIG. 10B shows a second diagram of measurement beam paths for the refraction measurement using the optical system shown in FIGS. 8A and 8B for patients' eyes with different spherical equivalents of the ametropia.
Figure 10C:
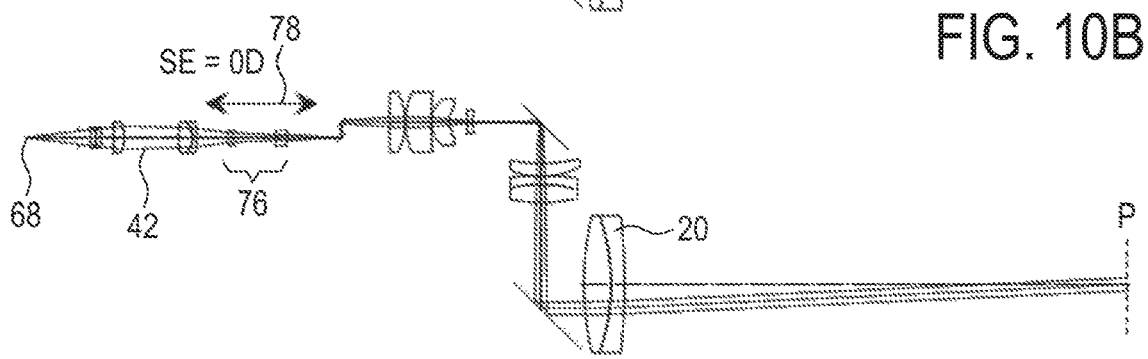
FIG. 10C shows a third diagram of measurement beam paths for the refraction measurement using the optical system shown in FIGS. 8A and 8B for patients' eyes with different spherical equivalents of the ametropia.
Figure 10D:
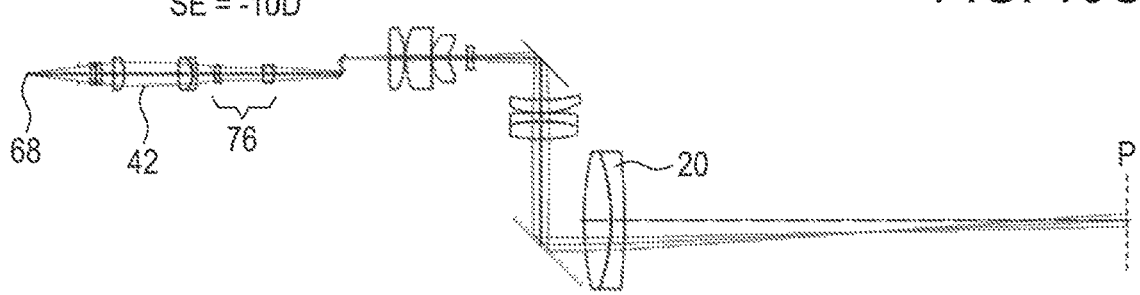
FIG. 10D shows a fourth diagram of measurement beam paths for the refraction measurement using the optical system shown in FIGS. 8A and 8B for patients' eyes with different spherical equivalents of the ametropia.
Figure 10E:
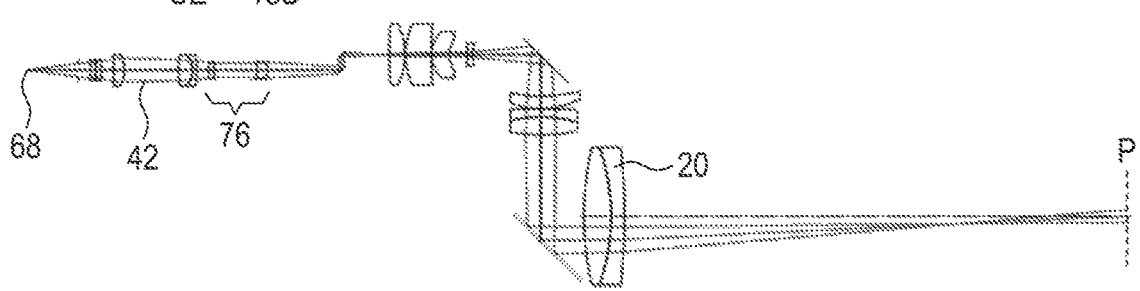
FIG. 10E shows a fifth diagram of measurement beam paths for the refraction measurement using the optical system shown in FIGS. 8A and 8B for patients' eyes with different spherical equivalents of the ametropia.

FIGS. 9A to 9C show various beam paths through the system 40/120. FIG. 9A shows the use of the system 40/120 as a refractometer 40, in which the measurement beam path 42 passes through the optical unit 60 including the main objective lens 20 of the surgical microscope 10, wherein the optical element 132 has been removed from the beam path. The intended position of the pupil P of the eye 12 of the patient is shown as a dashed line. FIG. 9A shows the telescope 76 in a displacement position corresponding to the spherical equivalent SE=0 D.

FIG. 9C shows the OCT beam path 130 in different positions of the scanning mirror 128 of the scanning mirror arrangement 124 for recording an OCT scan of the anterior chamber of the patient's eye 12. The adaptive component 74 for compensating an astigmatism, through which the OCT beam path passes, is in the neutral position in this case. By scanning using the scanning mirror arrangement 124, it is possible to record a 3D data cube of the patient's eye 12 in the region of the anterior chamber of eye. Here, the adjustable telescope 76 can also be used to focus the OCT beam path in the region of the anterior chamber of the eye.

FIG. 9B shows the OCT beam path 130 in different positions of the scanning mirror 128 of the scanning mirror arrangement 124 for recording an OCT scan of the retina 16 of the patient's eye 12. The adaptive component 74 for compensating an astigmatism is in the neutral setting in this case. The OCT beam path between the end 70 of the optical fiber 68 and the main objective lens 20 is unchanged in relation to the right partial image; however, a fundus imaging system 138, including a reduction optical unit 140 and an ophthalmoscope loupe 142, is introduced into the OCT beam path between the main objective lens 20 and the eye 12. Using the fundus imaging system 138, it is possible to focus the OCT measurement light onto the retina 16. A point between the two scanning mirrors 126 and 128 is imaged in the vicinity of the iris of the patient's eye 12 by the fundus imaging system 138 such that the OCT measurement light can pass unblocked through the patient's pupil P independent of the positioning of the scanning mirrors 126 and 128. Then, the OCT beam path 130 can be focused either using the displaceable telescope 76 for compensating the spherical equivalent or using the fundus imaging system 138, should the latter include a displaceable focusing lens.

FIGS. 10A to 10E show the optical system 40/120 with the optical element 132 not located in the measurement beam path 42, for the purposes of measuring refraction on patients' eyes with a different spherical equivalent SE and corresponding different settings (displacement positions) of the telescope 76 for compensating the spherical equivalent SE. The corresponding spherical equivalent SE to be compensated is described in the respective FIGS. 10A to 10E.

One of the two scanning mirrors 126, 128, or both, may optionally vibrate back and forth by a small angle to generate a movement of the light spot 46 (FIG. 1) on the retina 16. Consequently, the scanning mirror arrangement 124 can advantageously be used instead of the above-described measures for moving the light spot 46 on the retina, and so the above-described measures for moving the light spot 46 can be dispensed with.

An ophthalmic surgical microscope 10 includes an optical system 40/120 according to the exemplary embodiment shown in FIGS. 8A to 10E can be provided in cost-effective fashion in the following configuration levels:

Configuration level 1: An ophthalmic surgical microscope 10 with a refractometer 40 according to the exemplary embodiment shown in FIGS. 8A to 10E without an additional optical element 132 such that the surgical microscope 10 facilitates the refraction measurement on the confocal principle. Here, the two scanning mirrors 126 and 128 may optionally be replaced by more cost-effective folding mirrors or may be completely dispensed with.

Configuration level 2: An ophthalmic surgical microscope 10 including an OCT system 120 according to the exemplary embodiment shown in FIGS. 8A to 9C with a fixedly installed additional optical element 132 facilitating the recording of OCT scans, both of the anterior chamber (FIG. 9C) and of the retina 16 (FIG. 9B).

Configuration level 3: An ophthalmic surgical microscope 10 including a refractometer 40/OCT system 120 with an introducible and removable optical element 132 facilitating both a refraction measurement and the recording of OCT scans.

The configuration levels 1 to 3 described above can be generated cost-effectively as they include many repeated parts and also use the same opto-mechanism (lens mounts, mirror holders, etc.).

Figure 11:
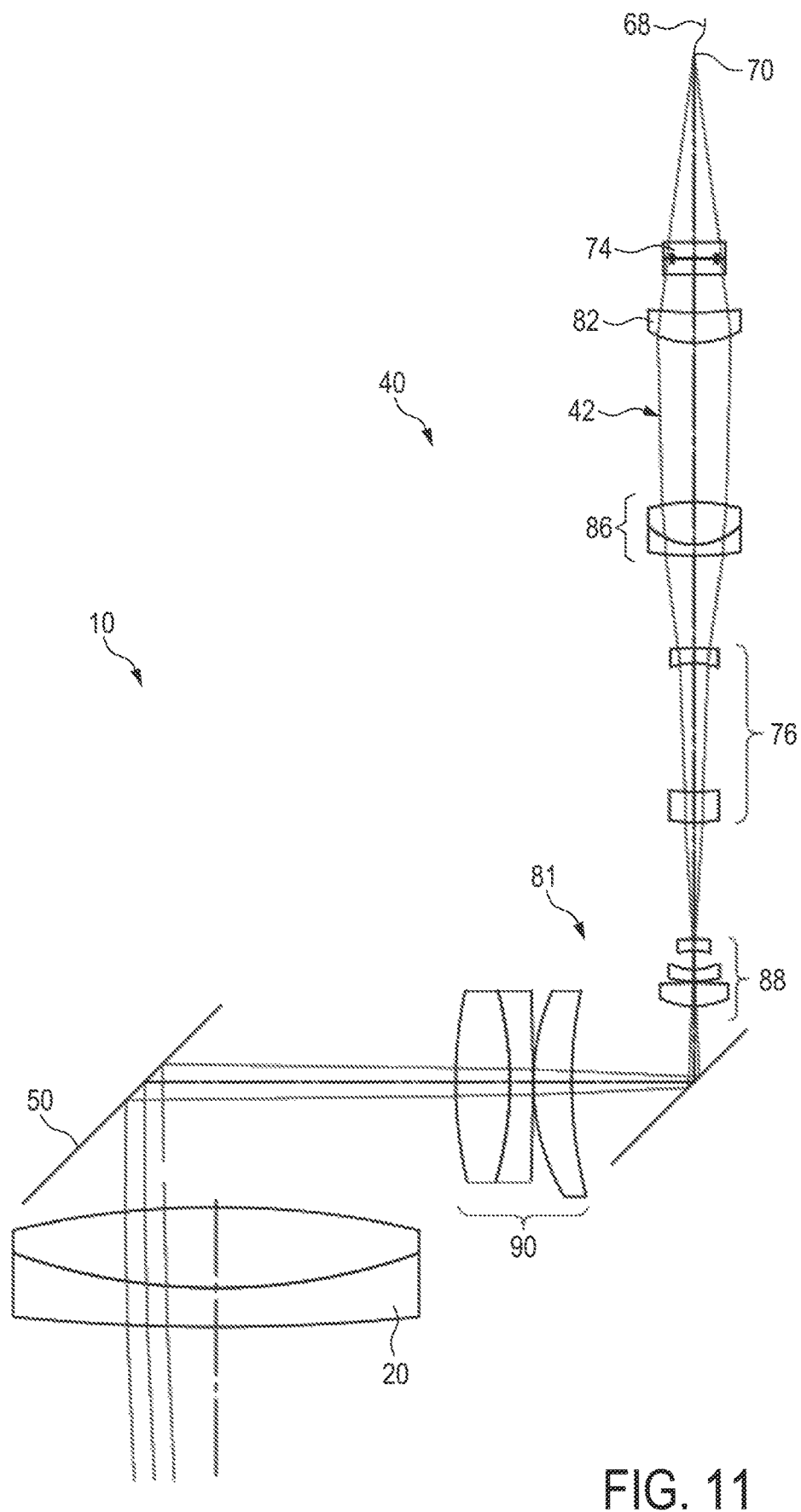
FIG. 11 shows a further exemplary embodiment of an ophthalmic surgical microscope including an optical system configured for a refraction measurement, wherein only the main objective lens is shown from the remaining components of the surgical microscope.

FIG. 11 shows a further exemplary embodiment of a surgical microscope 10. For simplification, in FIG. 11 the same reference signs were used as in FIGS. 1 to 10E for elements that are identical, similar or comparable to elements in FIGS. 1 to 10E. Like in the preceding exemplary embodiments, the optical system 40 of FIG. 11 is integrated into the surgical microscope 10 of FIG. 1, of which only the main objective lens 20 has been shown in addition to the optical system 40. The optical system 40 configured as a confocal refractometer is suitable for use in the surgical microscope 10 shown FIG. 1 if the latter should not or need not include an OCT system. The additional introducible and removable optical element 132 is dispensed with in the exemplary embodiment shown in FIG. 11.

The structure of the refractometer 40 shown in FIG. 11 differs from the structure of the refractometer 40 shown in FIG. 8A in terms of the lens group 88 of the second optical arrangement 81, which has negative refractive power in the exemplary embodiment shown in FIG. 11 and which forms a Galilean telescope with the lens group 90 in order to realize a more compact installation space.

The exemplary embodiment of the refractometer 40 shown in FIG. 11 shows how it is possible to cost-effectively offer a surgical microscope 10 in various exemplary embodiments, with the exemplary embodiment without OCT system being particularly compact. Here, a surgical microscope 10 including the refractometer 40 shown in FIG. 11 may represent the aforementioned configuration level 1 of an ophthalmic surgical microscope 10 if a particularly compact structure of the surgical microscope 10 including a refractometer 40 is desired.

An exemplary embodiment of a surgical microscope 10 including an integrated optical system 40/120 that can selectively be operated as a confocal refractometer and as an OCT system and that is modified with respect to the exemplary embodiment shown in FIGS. 8A to 10E is described with reference to FIGS. 12A to 18E. Only the main objective lens 20 of the surgical microscope 10 is shown in addition to the optical system 40/120. In FIG. 11, the same reference signs are used as in FIGS. 8A to 10E for elements that are identical, similar or comparable to elements shown in FIGS. 8A to 10E.

The confocal optical system 40/120 includes a zoomable collimator 150. The zoomable collimator 150, which collimates the measurement light beam 44 emerging from the end 70 of the optical fiber 68, has a variable focal length. In FIGS. 13A to 13D, the zoomable collimator 150 is illustrated on its own and in magnified fashion in relation to FIGS. 12A and 12B. The zoomable collimator 150 comprises three lenses 152, 154, and 156, which are schematically shown as lines in FIGS. 13A to 13D. By way of example, the focal lengths of the lenses 152, 154, and 156 are $f_1=+8.188$ mm (lens 152), $f_2=-4.067$ mm (lens 154) and $f_3=+19.15$ mm (lens 156). FIGS. 13A to 13D show a zoomable collimator 150 in four different zoom settings. The zoomable collimator 150 can be used to vary the beam diameter of the measurement light beam 44 at the eye 12 of the patient during the refraction measurement in the case of a constant aperture of the measurement light beam 44 emerging from the optical fiber 68, with the light energy striking the eye 12 however remaining constant. This is advantageous over the exemplary embodiments shown in FIG. 8 and in FIG. 3, in which provision is made of a stop 96 with a changeable aperture cross section for varying the beam diameter of the measurement light beam 44 at the eye 12; this is accompanied by a certain loss of luminous power when the stop 96 is constricted for reducing the beam diameter. Moreover, the exemplary embodiment of the surgical microscope 10 shown in FIGS. 12A and 12B is advantageous in that the measurement light 48 reflected back from the retina 16 can be optimally coupled back into the optical fiber 68 such that a higher used signal can be measured.

Figure 12A:
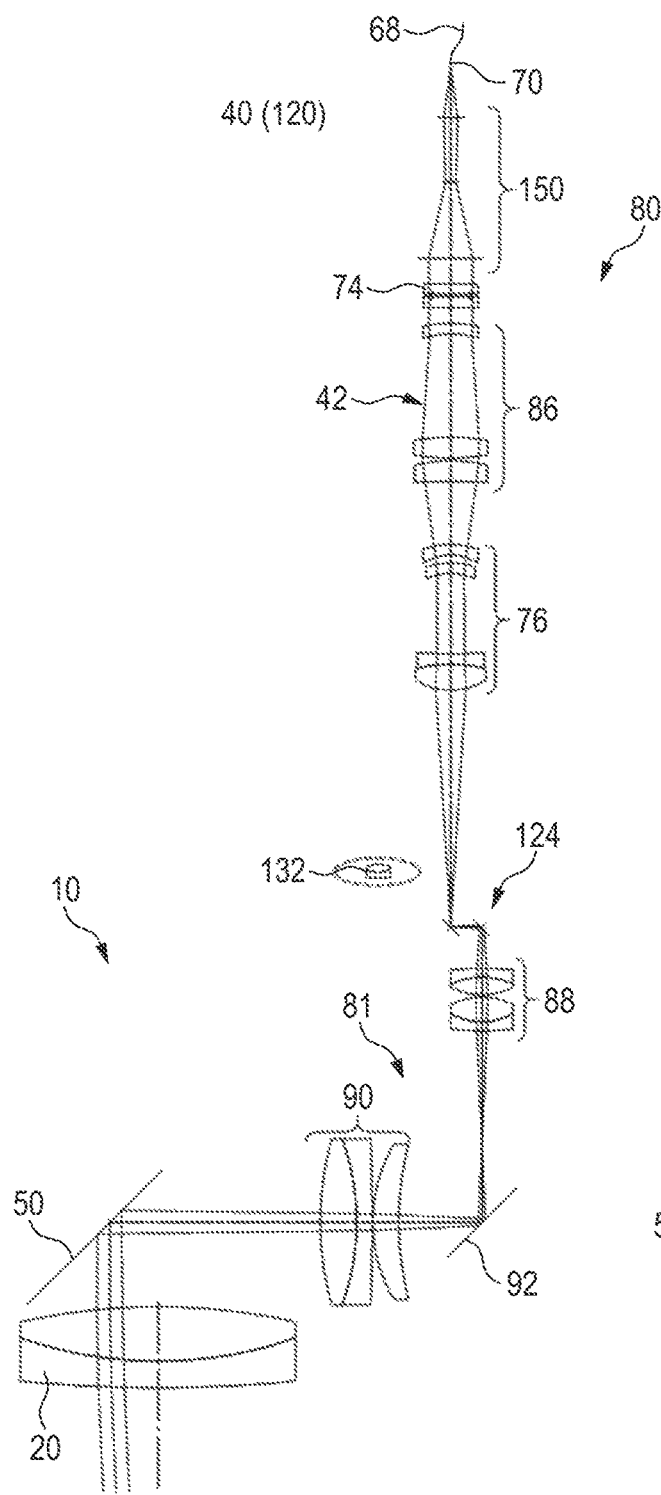
FIG. 12A shows a measurement beam path for the refraction measurement according to a further exemplary embodiment of the ophthalmic surgical microscope.
Figure 12B:
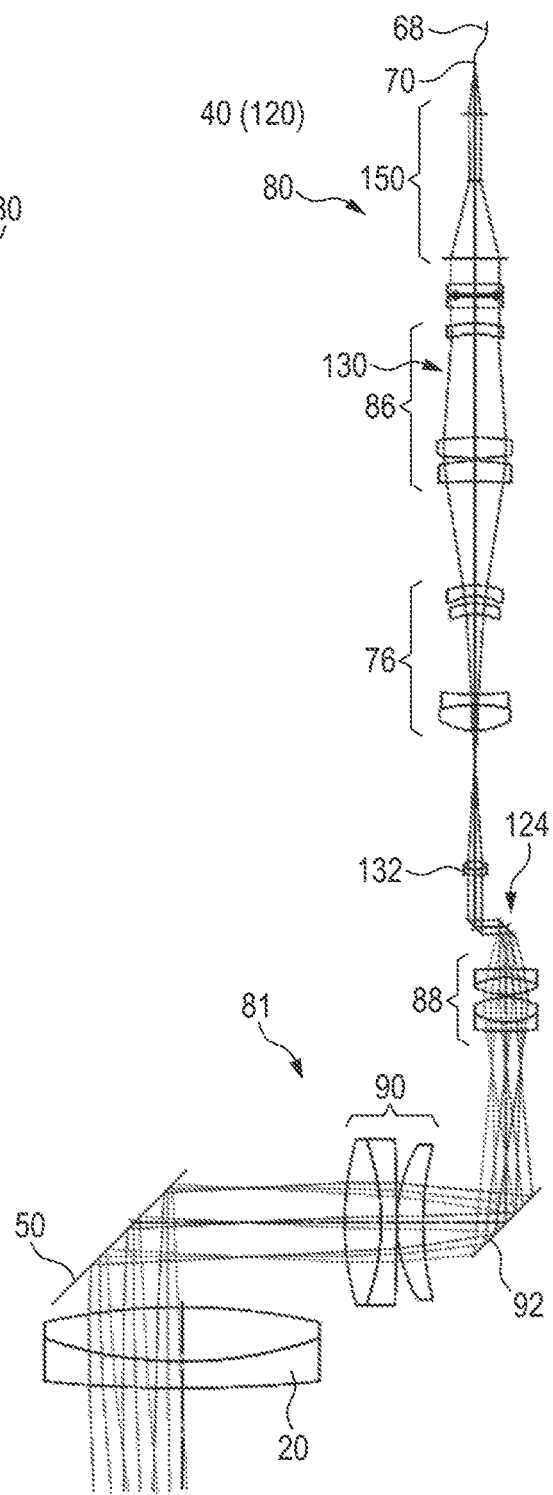
FIG. 12B shows an OCT beam path for recording an OCT scan according to a further exemplary embodiment of the ophthalmic surgical microscope.
Figure 13A:
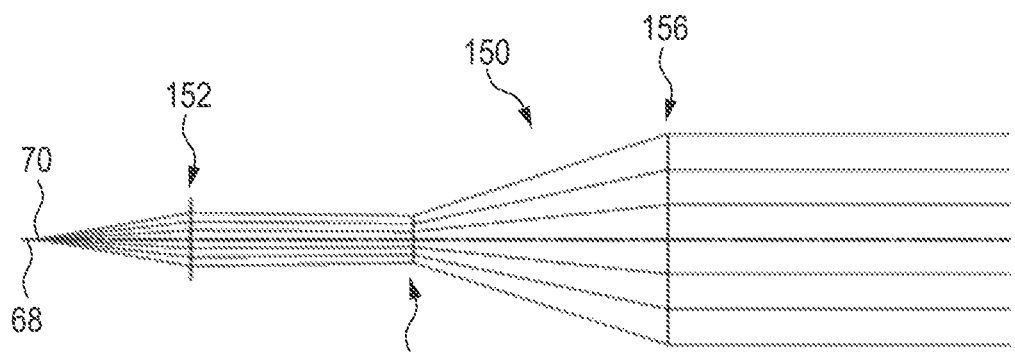
FIGS. 13A to 13D show beam paths through the collimator in four different zoom positions of the collimator of the optical system of the surgical microscope shown in FIGS. 12A and 12B.
Figure 13B:
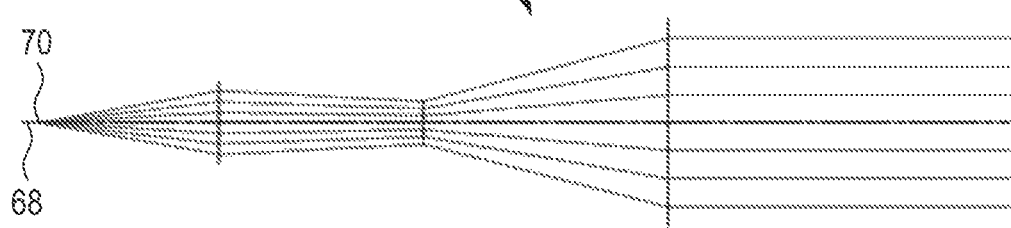
Figure 13C:
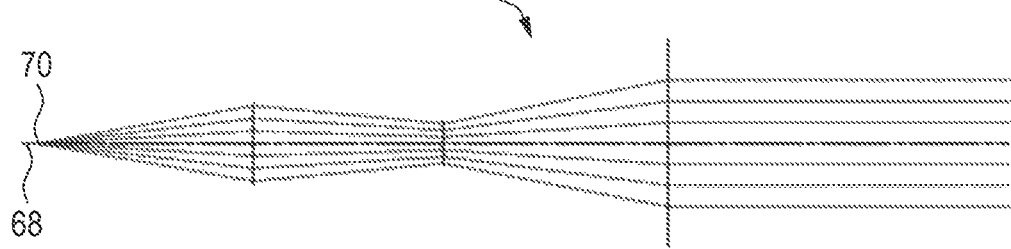
Figure 13D:
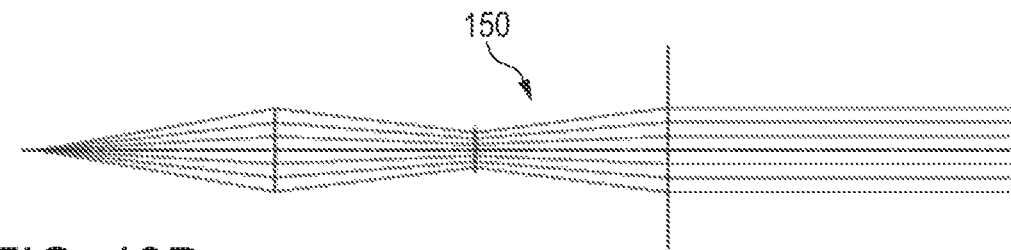

While the optical system 40/120 is shown as a confocal refractometer 40 with the measurement beam path 42 for measuring refraction in FIG. 12A, FIG. 12B shows the optical system 40/120 as an OCT system 120 with an OCT beam path 130 for recording an OCT scan, wherein an additional optical element 132 has been introduced into the OCT beam path in the system 40/120 to this end. The aperture of the OCT measurement beam, and hence its Rayleigh range in the object space (eye 12), can be varied with the aid of the zoomable collimator 150 when recording OCT scans. The Rayleigh range is a measure for the optical depth of field. If the Rayleigh range is varied, this facilitates matching of the optical depth of field to the OCT scanning depth, which is predetermined by the spectral width of the OCT measurement light, for example.

A further advantage of the exemplary embodiment shown in FIGS. 12A and 12B is that the end 70 of the optical fiber 68 is fixed when zooming the collimator 150, and so the optical path length from the end 70 of the optical fiber 68 to the patient's eye 12 is independent of the focal length of the zoomable collimator 150 that was set during the OCT scan. Moreover, a fixed end of the optical fiber 68 is advantageous since the movement of the optical fiber 68 can damage the latter.

A further difference between the exemplary embodiment shown in FIGS. 12A and 12B and the preceding exemplary embodiments is that the adaptive component 74 for compensating the astigmatism is arranged downstream of the collimator 150, as seen from the end 70 of the optical fiber 68, as a result of which the adaptive component 74 is arranged in the parallel beam path. This is advantageous in that even in the neutral setting of the adaptive component 74, in which residual aberrations may occur, are minimized.

The adaptive component 74 is located in the focal plane of the lens group 86. This ensures that the adaptive component 74 is always imaged in the pupil plane P of the eye 12, even if the telescope 76 for compensating the spherical equivalent is adjusted.

Figure 14A:
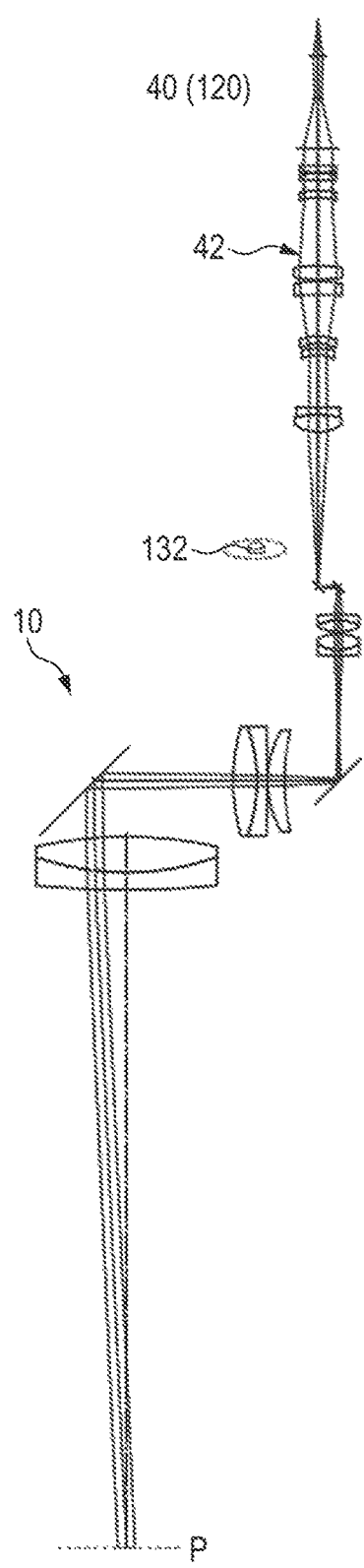
FIG. 14A shows a measurement beam path for the refraction measurement of the exemplary embodiment shown in FIG. 12A.

Similar to FIGS. 9A to 9C, FIGS. 14A to 14C show various measurement and OCT beam paths 42 and 130 for the exemplary embodiment shown in FIGS. 12A and 12B. FIG. 14A shows the system 40/120 with the measurement beam path 42 for the refraction measurement, with the additional optical element 132 having been removed from the measurement beam path. A refraction measurement of the eye 12 of the patient is carried out in this configuration by the confocal refractometer 40.

Figure 14B:
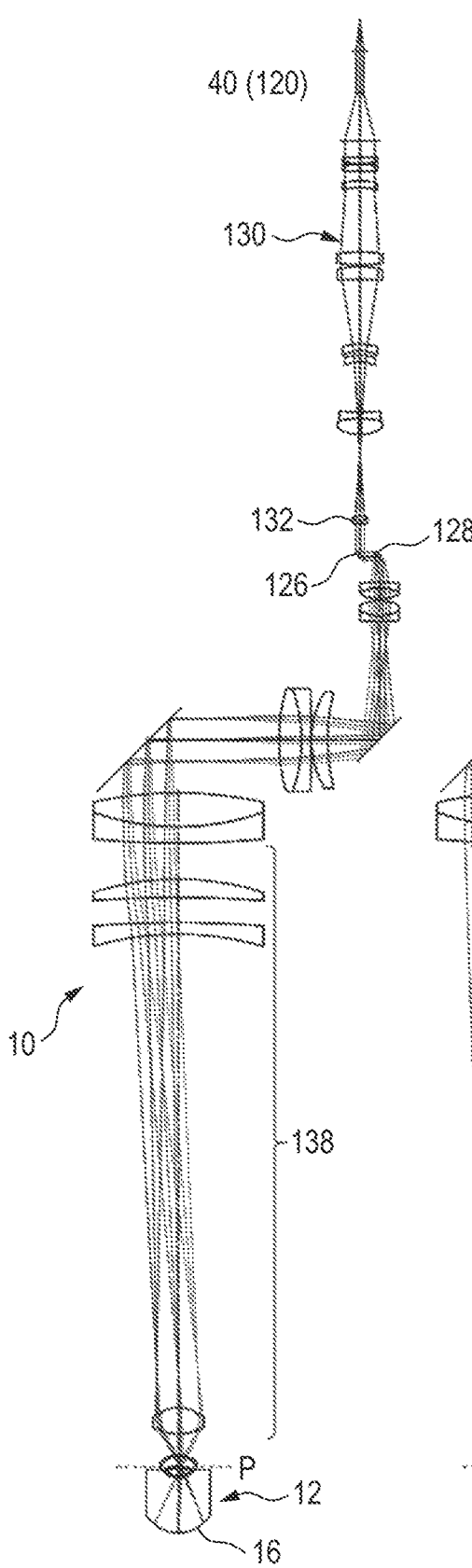
FIG. 14B shows an OCT beam path for recording an OCT scan of the retina.
Figure 14C:
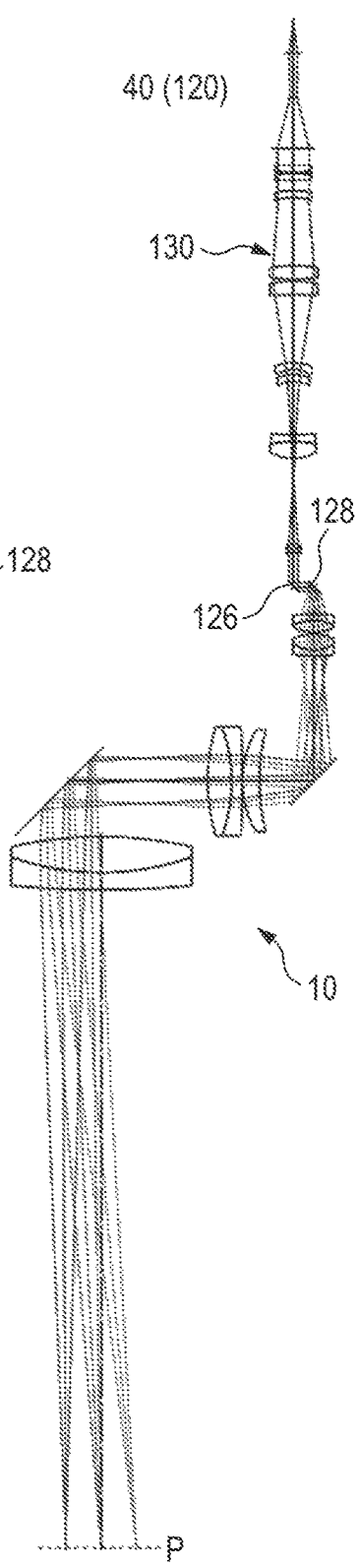
FIG. 14C shows an OCT beam path for recording an OCT scan of the anterior chamber.

In FIG. 14B, the additional optical element 132 and the fundus imaging system 138 have been introduced into the OCT beam path 130 such that an OCT scan of the retina 16 can be recorded. In FIG. 14C, the additional optical element 132, but not the fundus imaging system 138, has been introduced into the OCT beam path 130, and so an OCT scan of the anterior chamber of the patient's eye 12 can be recorded. Like previously for the representation of the OCT beam path, beam paths in different scanning positions of the scanning mirror 128 are plotted in the central and right partial image.

Figure 15:
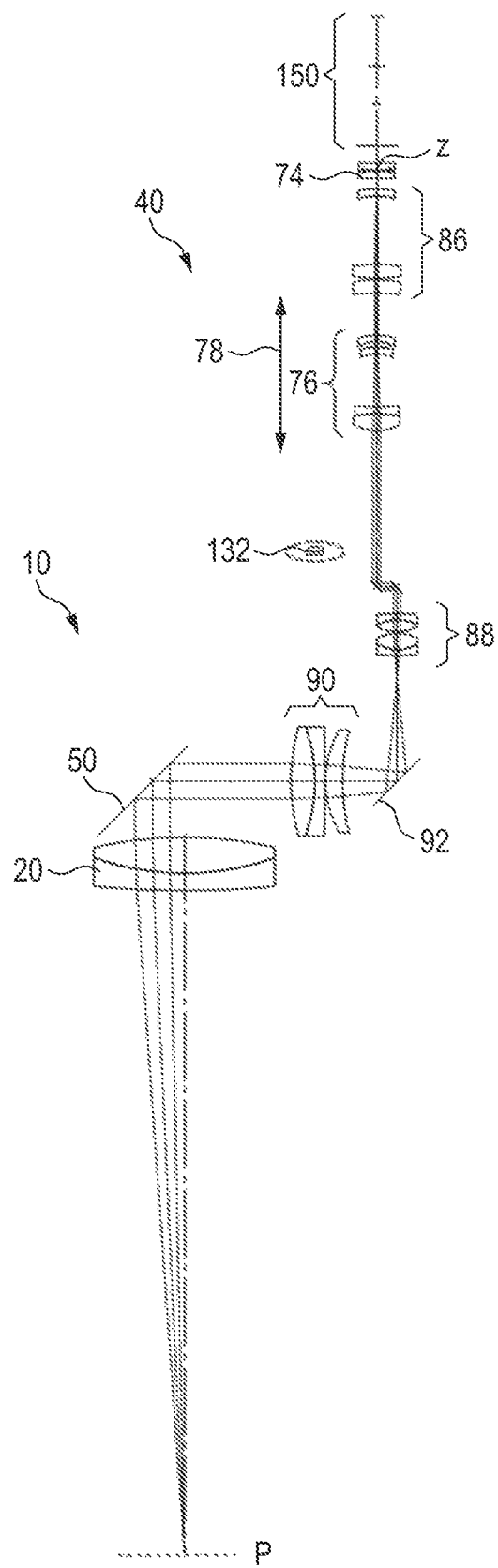
FIG. 15 shows FIG. 14A with a beam path for elucidating how an adaptive component for compensating an astigmatism is imaged into a pupil plane of a patient's eye.

FIG. 15 once again shows FIG. 14A on its own, with an imagined beam emanating from the center Z of the adaptive component 74 being shown here, as has already been explained above with regard to FIGS. 4A to 4D. FIG. 15 shows that the adaptive component 74 for compensating the astigmatism is imaged into the pupil plane P of the patient's eye 12.

Figures 16A, 16B, 16C:
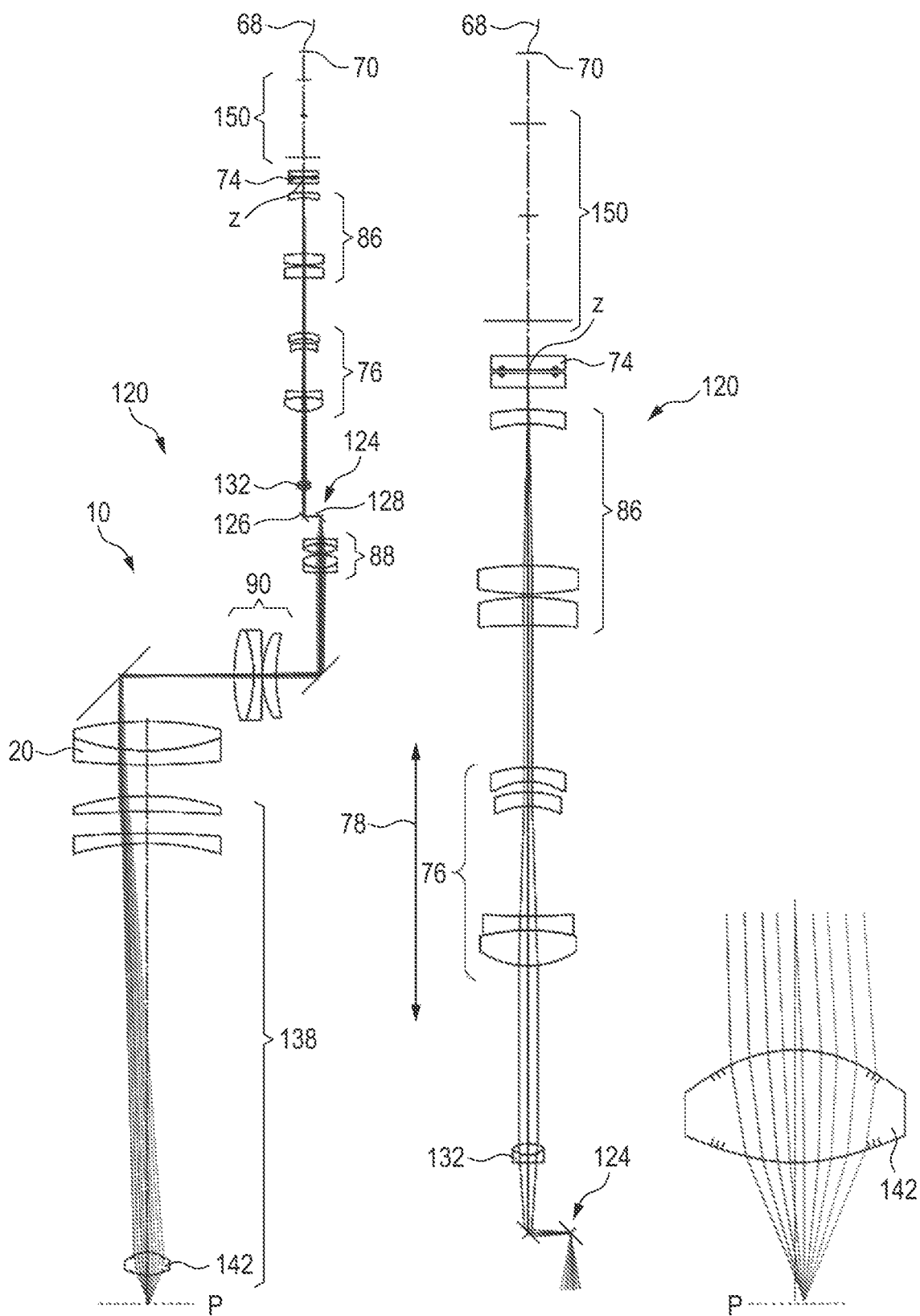
FIG. 16A shows FIG. 14B, wherein the beam path is shown for elucidating how the adaptive component for compensating an astigmatism is imaged into a pupil plane of the patient's eye during an OCT scan.
FIG. 16B shows a magnified section of FIG. 16B.
FIG. 16C shows an even more magnified section of FIG. 16A.
Figure 17A:
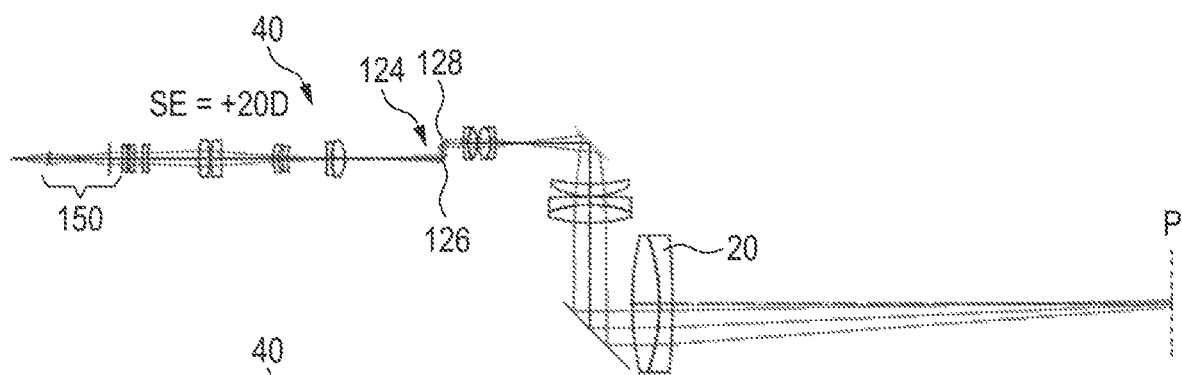
FIGS. 17A to 17E show five diagrams with measurement beam paths for the refraction measurement using the exemplary embodiment shown in FIGS. 12A and 12B for patients' eyes with different spherical equivalents of the ametropia and with a greater beam diameter of the measurement light beam at the patient's eye.
Figure 17B:
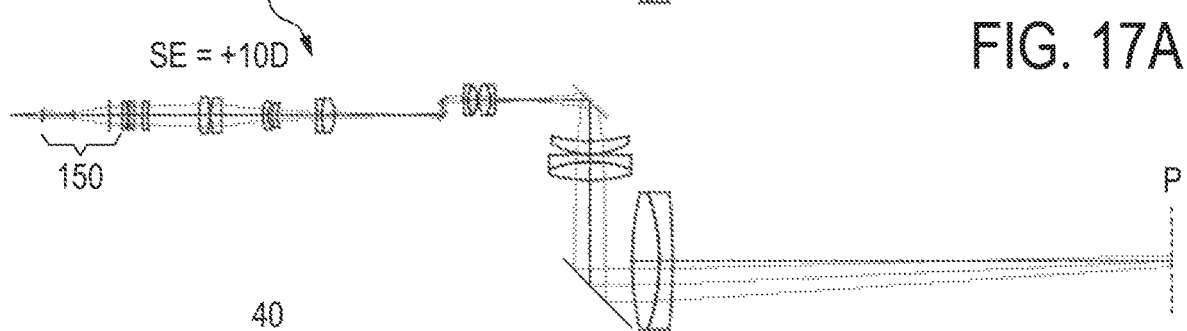
Figure 17C:
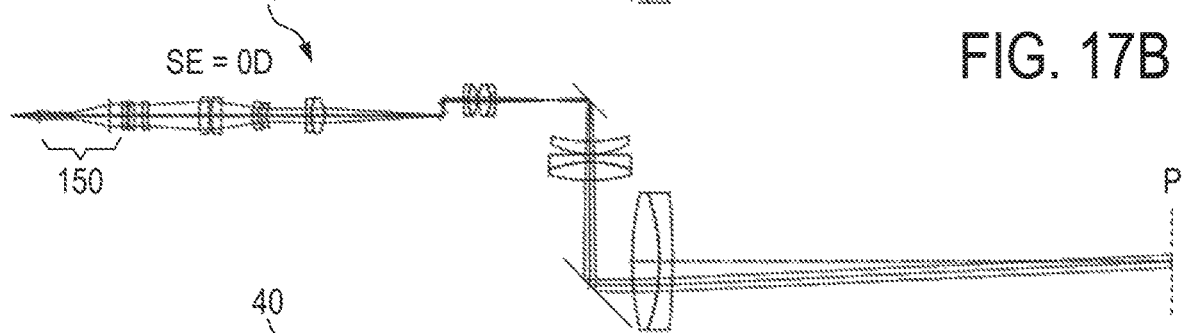
Figure 17D:
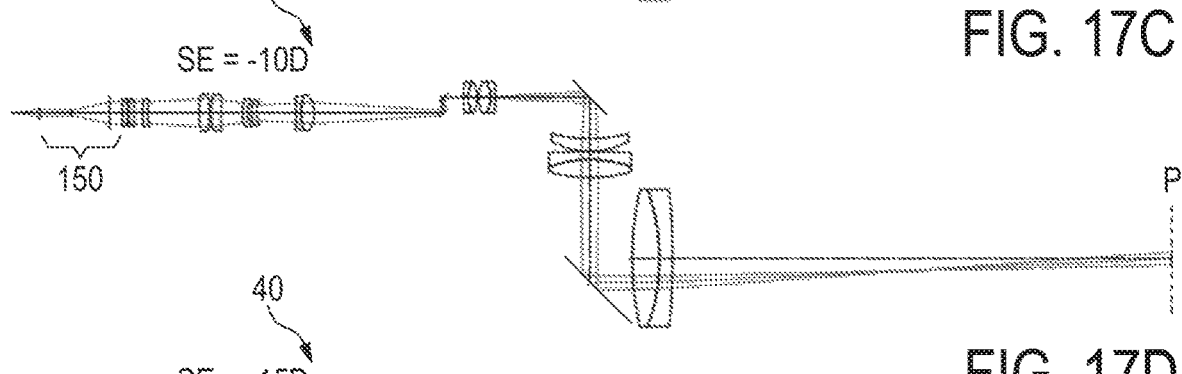
Figure 17E:
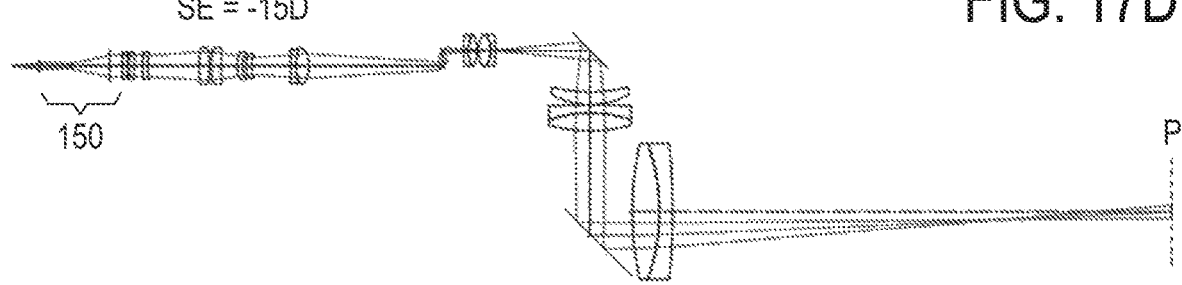
Figure 18A:
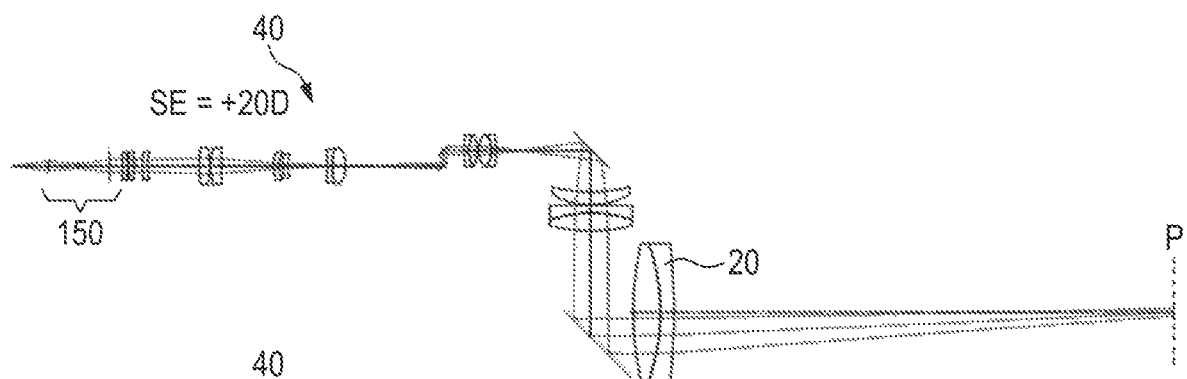
FIGS. 18A to 18E show five diagrams with measurement beam paths for the refraction measurement using the exemplary embodiment shown in FIGS. 12A and 12B for patients' eyes with different spherical equivalents of the ametropia and with a smaller beam diameter of the measurement light beam at the patient's eye.
Figure 18B:
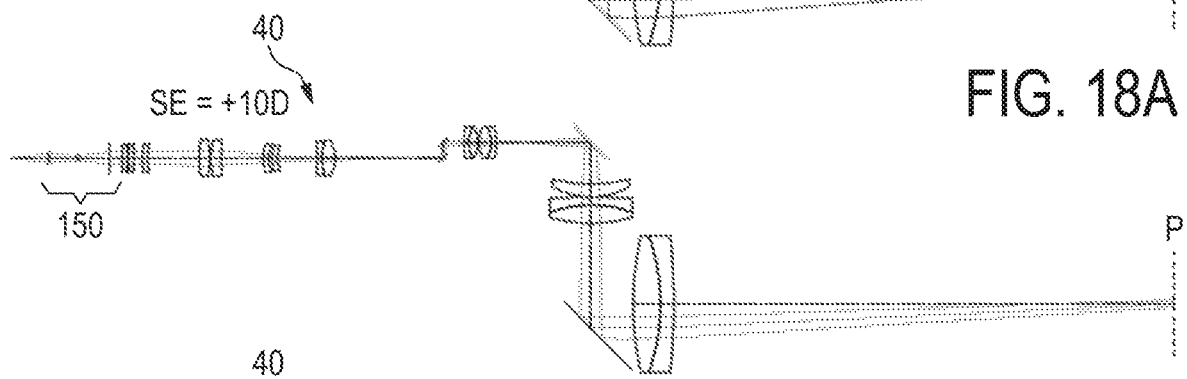
Figure 18C:
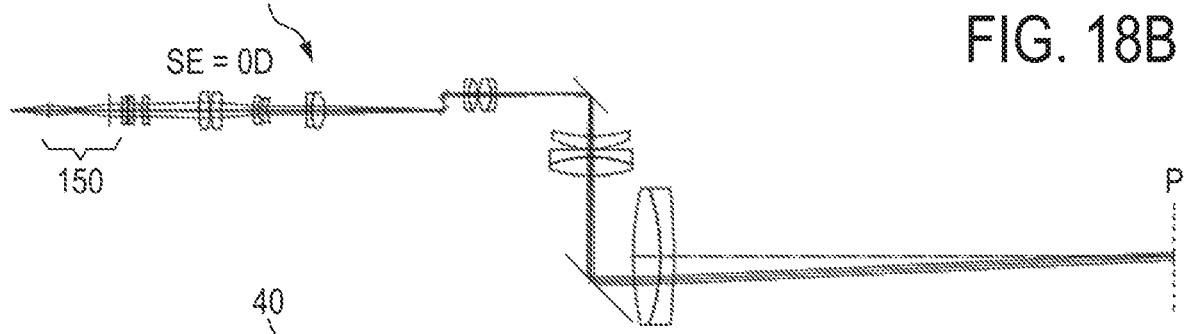
Figure 18D:
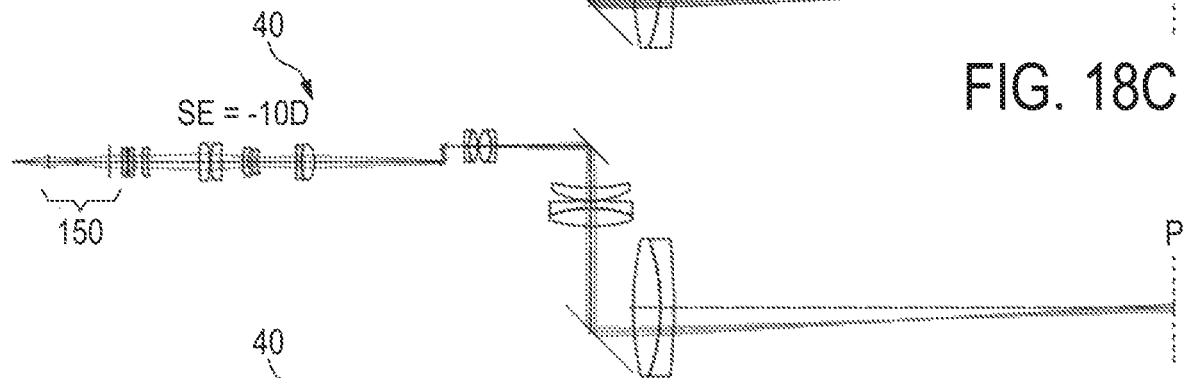
Figure 18E:
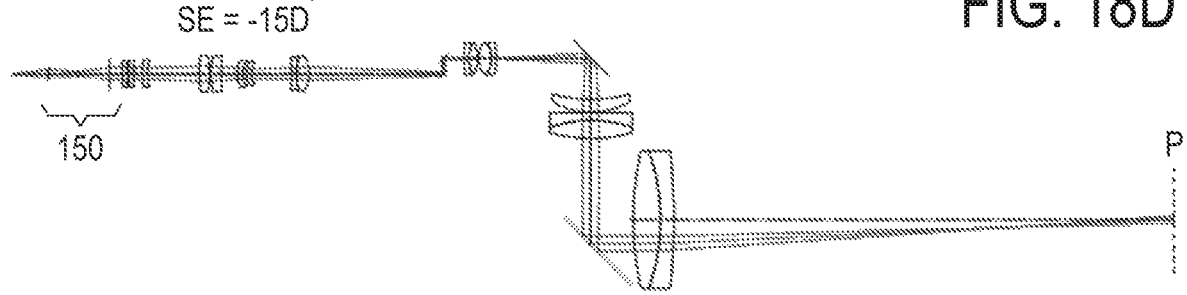

A further aspect of the use of the system 40/120 as an OCT system 120 is described with reference to FIGS. 16A to 16C. It is known that the quality of an OCT scan of the retina 16 is impaired if the patient's eye 12 has an astigmatism. The reason for this is that an astigmatism of the patient's eye 12, which is caused by a distortion of the cornea, for example, causes a deterioration in the imaging of the end 70 of the optical fiber 68 on the retina 16 and increases the associated light spot 46 on the retina 16. The exemplary embodiment shown in FIGS. 12A and 12B is advantageous in that the adaptive component 74 for the astigmatism can also be used to compensate the astigmatism of the patient's eye 12 when recording an OCT scan of the retina 16. This is achieved by virtue of the adaptive component 74 for the astigmatism being imaged on the patient's pupil P, even during the recording of an OCT scan of the retina 16. In turn, from a technical point of view, this is achieved by virtue of the additional optical element 132 having positive refractive power or focal length in this exemplary embodiment and being arranged in such a way that the focal plane thereof lies in the vicinity of the scanning mirror arrangement 124 or, more advantageously, between the scanning mirrors 126, 128. FIG. 16A shows that a point Z on the adaptive component 74 for the astigmatism is imaged on the patient's pupil P by the lens groups 88 and 90, the main objective lens 20 and the fundus imaging system 138 when recording of an OCT scan of the retina 16. Consequently, it is possible to compensate an astigmatism of the patient's eye 12 when recording an OCT scan of the retina by virtue of the adaptive component 74 for the astigmatism being set in suitable fashion in respect of the astigmatism C to be compensated and the axis position φ of the patient's eye 12. Consequently, an improvement is brought about in the imaging of the end 70 of the optical fiber 68 on the retina 16, with the imaging leading to a smaller light spot 46 on the retina 16. This allows more detailed information to be obtained about the retina 16, this being facilitated by recording the OCT scan of the retina 16.

FIG. 16B shows a magnified section of FIG. 16A in the region from the optical fiber 68 to the scanning mirror arrangement 124 and FIG. 16C shows an even further magnified section of FIG. 16A in the region of the ophthalmoscope loupe 142.

FIGS. 17A to 17E and 18A to 18E show the system 40/120 shown in FIGS. 12A and 12B when the latter is used as a confocal refractometer 40 for refraction measurements of patients' eyes 12 with different spherical equivalents of the ametropia. The different spherical equivalents SE are shown in FIGS. 17A to 17E and 18A to 18E. For the purposes of performing a refraction measurement, the additional optical element 132 is not located in the measurement beam path 42, as already described above. In FIGS. 17A to 17E, the focal length of the zoomable collimator 150 was set in such a way that the beam diameter of the patient's eye is 5 mm for spherical equivalents SE in the range of $-15\,\mathrm{D} < SE \lesssim +5\,\mathrm{D}$. In the case of hyperopic eyes with $SE \gtrsim +5\,\mathrm{D}$, the measurement beam path 42 may be vignetted at the scanning mirrors of the scanning mirror arrangement since the latter should have a scanning speed that is as high as possible for the OCT measurement and therefore cannot be chosen to be too large. Therefore, the focal length of the zoomable collimator 150 shown in FIGS. 18A to 18E is chosen in such a way in the case of hyperopic eyes with $SE \gtrsim +5\,\mathrm{D}$ the light beam of the measurement beam path just passes through the scanning mirrors 126 and 128 in non-vignetted fashion, and the beam diameter at the eye 12 is smaller at SE=+10 D and SE=+20 D, and is 4.2 mm and 2.6 mm, respectively.

Figure 19A:
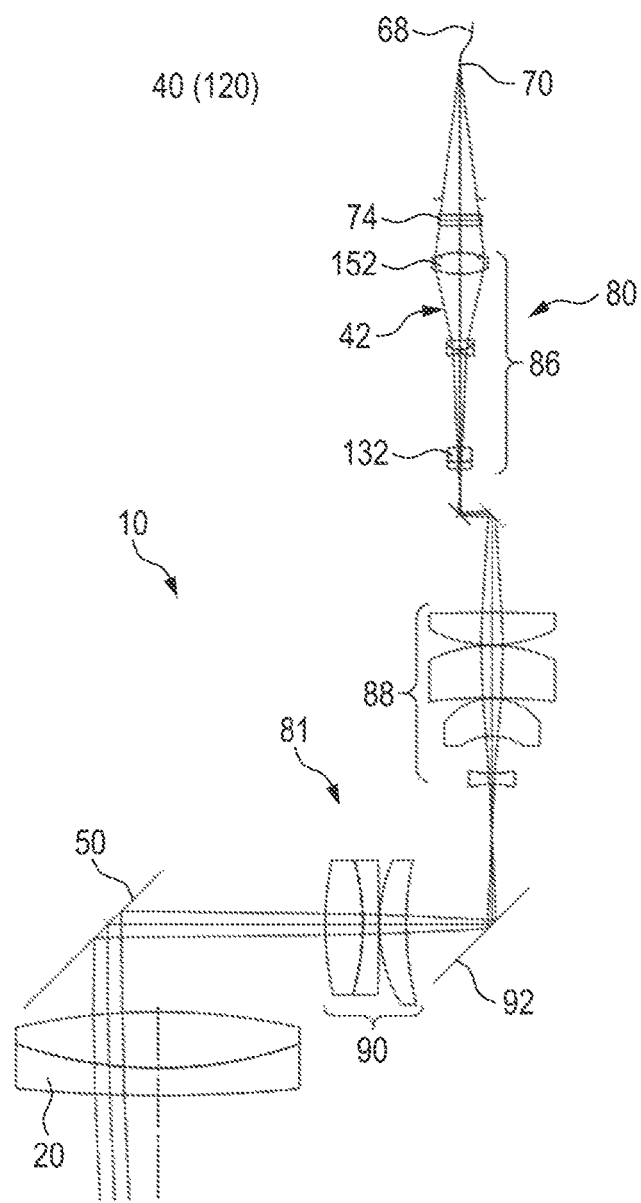
FIG. 19A shows a measurement beam path for the refraction measurement according to a further exemplary embodiment of an ophthalmic surgical microscope including an optical system, which is configured for refraction measurement and for recording an OCT scan.
Figure 19B:
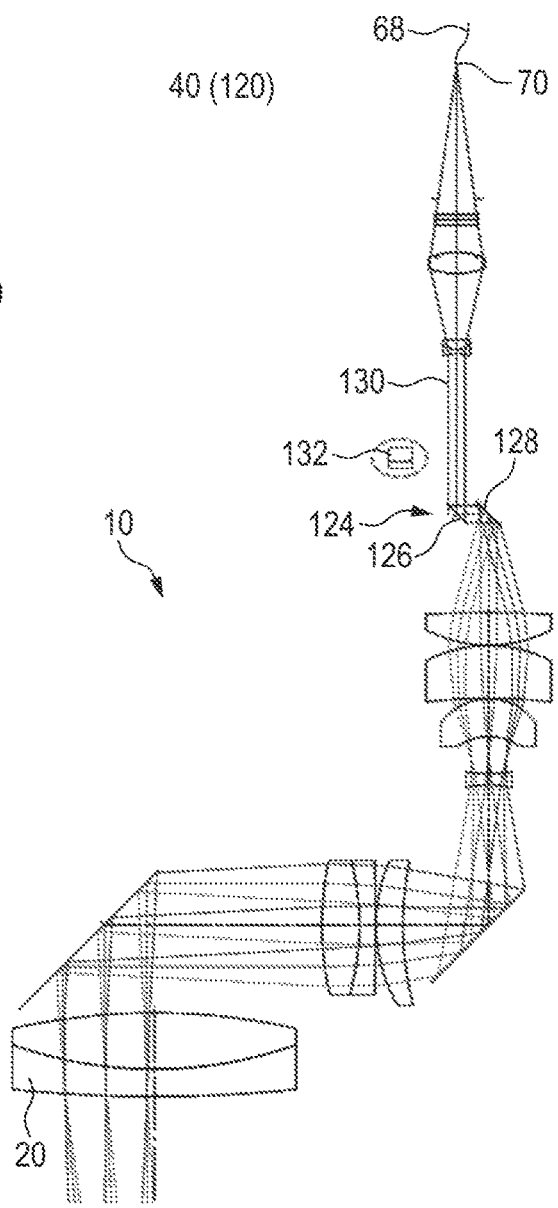
FIG. 19B shows an OCT beam path for recording an OCT scan according to the further exemplary embodiment of the ophthalmic surgical microscope.

An even further exemplary embodiment of an ophthalmic surgical microscope 10 including a confocal optical system 40/120, which is configured as a combined refractometer/OCT system 40, 120, is described with reference to FIGS. 19A to 21E. In addition to the optical system 40/120, only the main objective lens 20 of the surgical microscope 10 is shown. FIG. 19A shows the combined refractometer/OCT system 40/120 when used for a refraction measurement and FIG. 19B shows the refractometer/OCT system when used for recording an OCT scan.

While the adaptive component 74 for the astigmatism and the adjustable telescope 76 for the spherical equivalent together form the AOM in the previous exemplary embodiments, the adaptive component 74 forms the adaptive optical module on its own in the exemplary embodiment shown in FIGS. 19A to 21E. To this end, the adaptive component 74 not only generates astigmatic power by adjusting its optical properties but can also compensate the spherical equivalent of the ametropia of the eye 12 of the patient. In respect of the astigmatism, the adaptive component 74 can generate a cylindrical refractive power with any phase position.

FIG. 19A shows the measurement beam path 42 for a refraction measurement with a set spherical equivalent SE=0 D. The adaptive component 74 is located near the focal plane of the lens group 86 such that the adaptive component 74 is imaged at infinity by the lens group 86. The lens groups 88 and 90 form a telescope. However, the latter need not be adjustable since the spherical equivalent can be compensated by adjusting the adaptive component 74.

The pupil P of the patient's eye 12 is located, once again, in the vicinity of the focal plane of the main objective lens 20. Consequently, the adaptive component 74 is virtually in a plane conjugate to the pupil P (FIGS. 20A and 20B) of the patient's eye 12, with the imaging scale β for imaging the adaptive component 74 on to the patient's pupil P being≈0.6.

The lens group 86 includes an optical element 132 that is introducible into the beam path and removable therefrom again; said optical element is introduced into the measurement beam path 42 when the system is used as a refractometer, while it is removed from the OCT beam path 130 when the system is used as an OCT system 120. The splitter mirror 92 is optionally provided, with reference being made to the description of FIG. 3.

Figure 20A:
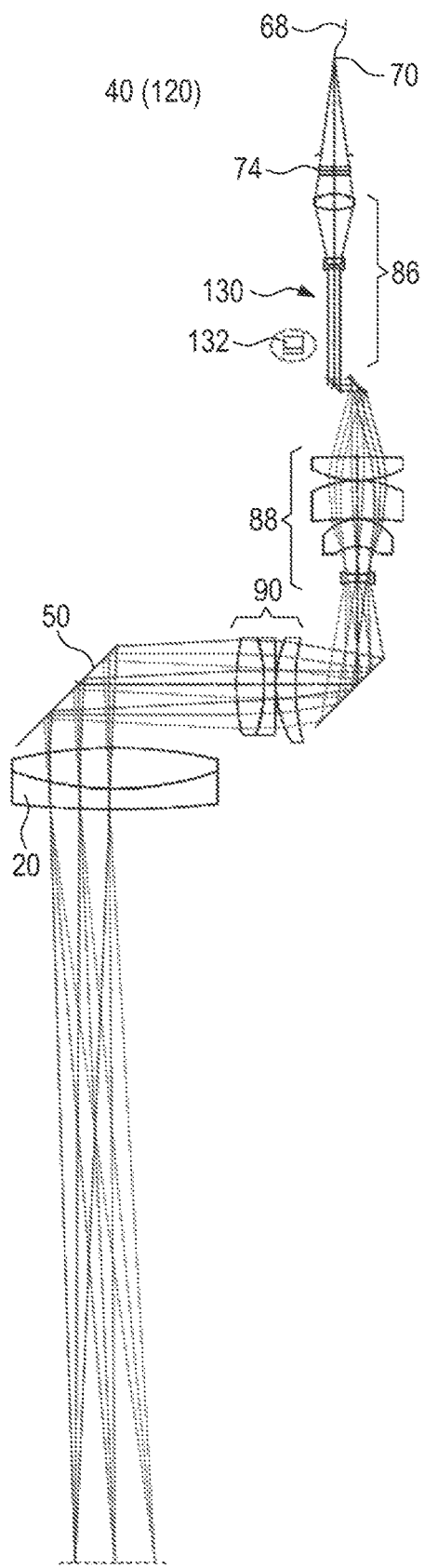
FIGS. 20A and 20B show FIGS. 19A and 19B, respectively, with complete beam paths up to the eye of the patient.

FIG. 19B and FIG. 20A show the use of the optical system 40/120 as an OCT system 120 for recording an OCT scan of the anterior chamber of the eye. In the shown case of recording an OCT scan, the spherical refractive power set at the adaptive component 74 is approximately −5.07 D such that the OCT light emerging from the end 70 of the optical fiber 68 strikes the scanning mirrors 126 and 128 of the scanning mirror arrangement 124 in virtually collimated fashion. The OCT beam path 130 can be focused in the region of the anterior chamber of the patient's eye by varying the spherical refractive power of the adaptive component 74. The lens group 86 includes an aspherical single lens 152; however, the latter can also be replaced by a cemented member.

Figure 20B:
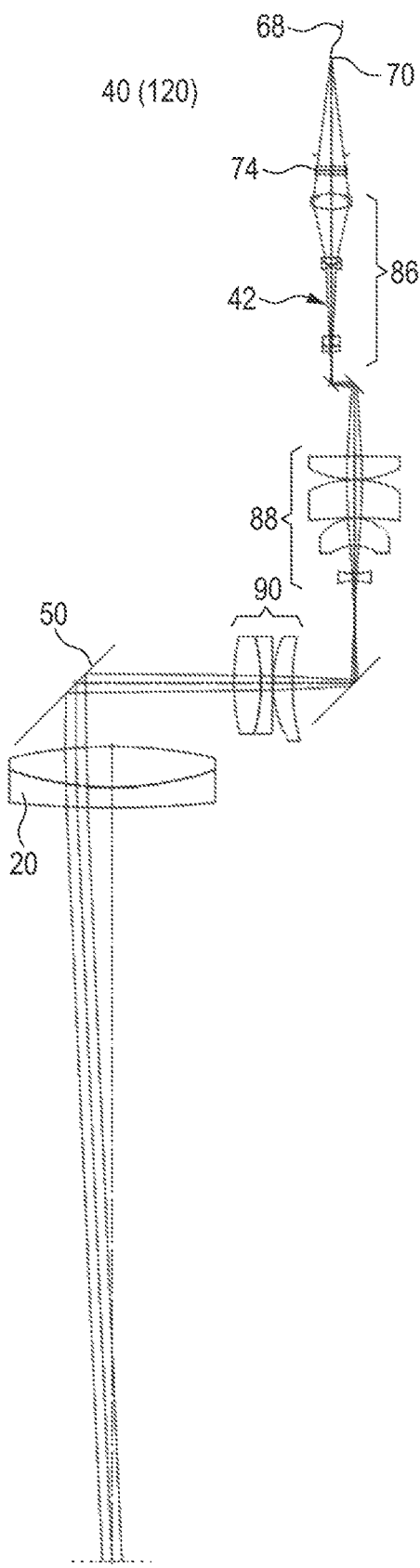
Figure 21A:
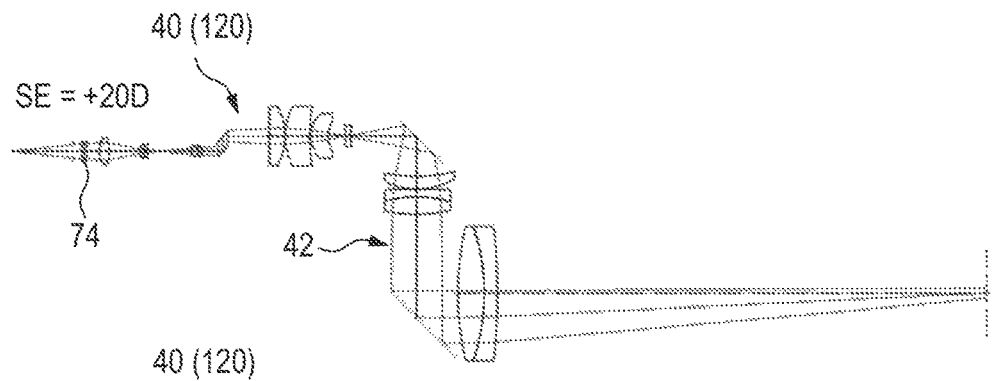
FIGS. 21A to 21E show five diagrams of measurement beam paths for the refraction measurement according to the exemplary embodiment shown in FIGS. 19A and 19B for patients' eyes with different spherical equivalents of the ametropia.
Figure 21B:
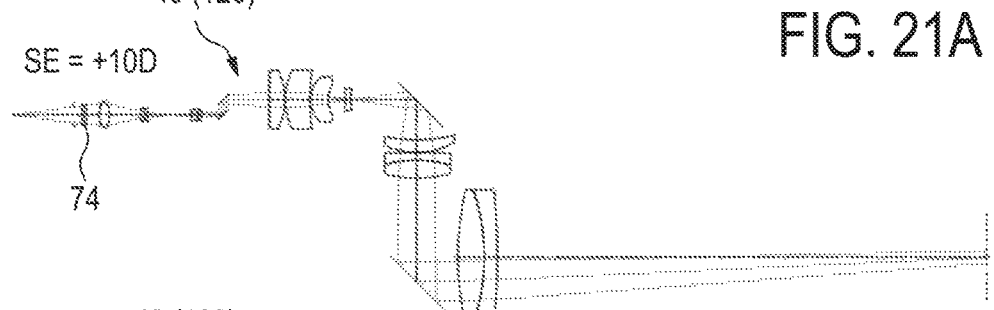
Figure 21C:
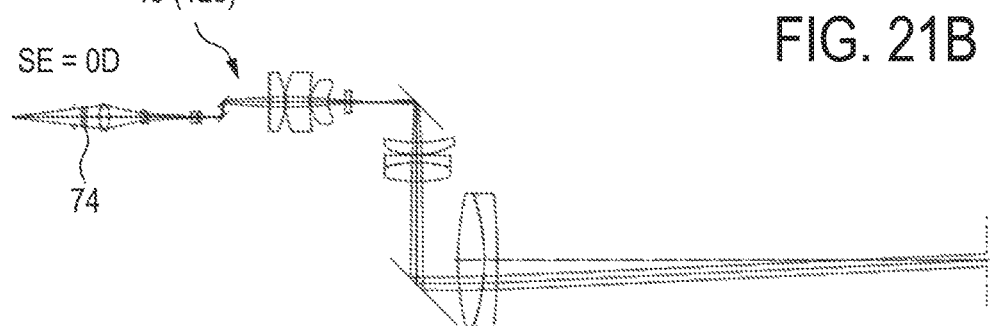
Figure 21D:
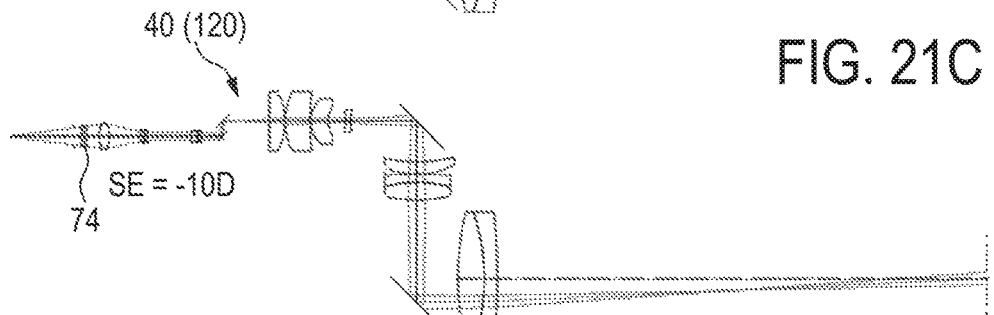
Figure 21E:
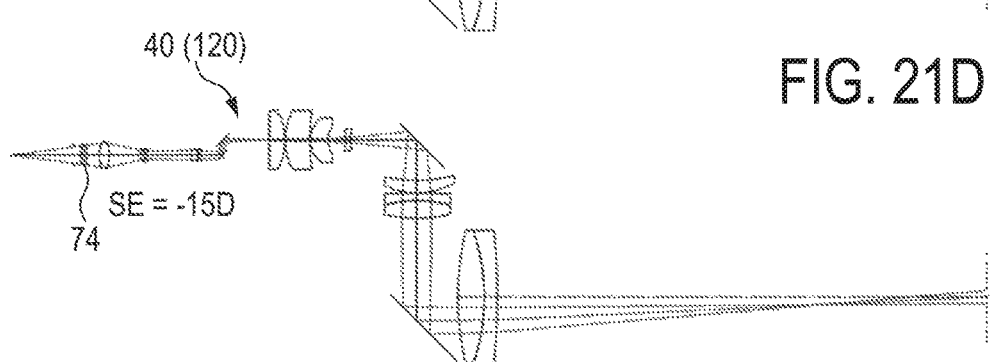

FIG. 20B shows the system 40/120 when used for the refraction measurement with a complete measurement beam path 42 from the end 70 of the optical fiber 68 up to the pupil plane P of the patient's eye 12. FIGS. 21A to 21E show various measurement beam paths 42 when using the system 40/120 as a refractometer 40. The various measurement beam paths 42 relate to different spherical equivalents SE of patients' eyes 12, with the spherical equivalents SE being specified in FIGS. 21A to 21E.

Here, the spherical refractive powers set at the adaptive component 74 are +9.451 D (SE=+20 D), +4.740 D (SE=+10 D), 0 D (SE=0 D), −4.769 D (SE=−10 D) and −7.165 D (SE=−15 D). For the relationship between the spherical equivalent SE to be compensated or the astigmatism C of the patient's eye and the spherical refractive power Φ and the cylindrical refractive power $C_{74}$ of the adaptive component 74, the following relationship applies approximately: $\Phi = \beta^2 \cdot SE$ and $C_{74} = \beta^2 \cdot C$, where $C_{74}$ represents the cylindrical refractive power of the adaptive component 74 in diopter. By way of example, the exact relationships between the refractive power Φ and the spherical equivalent SE, or between the astigmatism C of the patient's eye and the cylindrical refractive power $C_{74}$ of the adaptive component 74 can be stored in a lookup table. Thus, for the purposes of measuring the patient's eye 12, the refractive power Φ, the cylindrical refractive power $C_{74}$ and the axis position of the adaptive component 74 are varied until the intensity of the reflected measurement light 48, coupled back into the optical fiber 68, is maximal at the light detector 56. Subsequently, the refractive error of the patient's eye 12 can be determined from the lookup table.

An advantage of the exemplary embodiment shown in FIGS. 19A to 21E is that there are no displaceable telescopes whose position has to be determined with great precision, the implementation of which requiring installation space and causing higher costs. Instead, an adaptive component 74 that renders the three parameters of spherical refractive power, cylindrical refractive power and cylinder axis position modifiable is required in the exemplary embodiment Shown in FIGS. 19A to 21E.

According to an exemplary embodiment, an adaptive component 74 includes the adaptive component 74 including three tightly adjacent liquid-filled membrane lenses, wherein one membrane lens can generate spherical refractive power and the other two membrane lenses can generate astigmatic refractive power in any axis position, without a mechanical movement being necessary.

According to a further exemplary embodiment, the adaptive component 74 includes a liquid lens, for example a lens commercially available under the trademark Visayan 80S0 from Varioptik.

According to an even further exemplary embodiment, the adaptive component 74 can be used to adjust both spherical refractive power and cylindrical refractive power and the axis position thereof includes an adaptive lens that is composed of two thin glass windows (with the thickness of 150 μm), wherein a piezoelectric actuator ring is applied to each of these glass windows. The space between the windows is filled with a transparent liquid, for example a mineral oil. The first window is used to generate a spherical refractive power and an astigmatism, while the second window generates coma and secondary astigmatism.

According to yet another exemplary embodiment, the adaptive component 74 includes a combination of a spherical membrane lens with variable refractive power and a tightly adjacent Stokes lens including two rotatable cylindrical lenses, as has already been described above.

An even further exemplary embodiment of an adaptive component 74, which can compensate both the spherical equivalent of the ametropia and the astigmatism with any axis position, includes a pair of Alvarez plates, which generates a variable spherical refractive power in the case of a displacement in a first direction perpendicular to an optical axis and which generates a variable cylindrical refractive power in the case of a displacement in a second direction that is perpendicular to the first direction and to the optical axis. The Alvarez plate pair is rotated about the optical axis for the purposes of varying the axis position.

In the above-described exemplary embodiments, the separation mirror 50 is shown in the spatial vicinity of the main objective lens 20, wherein the observation beam path 18 and the measurement beam path 42 for the refraction measurement or the OCT beam path for the OCT measurement are separated from one another with the aid of the separation mirror 50. The separation layer 50 can be fully mirrored or else have different transmissions or reflections depending on the wavelength. By way of example, the separation mirror 50 can have a transmission T>85% for visual light and a reflection R>95% for light with a wavelength λ>700 nm. The separation mirror 50 can also be arranged below the main objective lens 20, as shown in FIG. 2. In this exemplary embodiment, too, sufficient working space remains for the surgeon above the patient's eye 12.

While the separation mirror 50 in the shown exemplary embodiment acts as a mirror for the measurement beam path 42 for the refraction measurement or for the OCT beam path 130 while the observation light is transmitted by the separation mirror 50 or runs past the latter, these beam paths could just as easily be interchanged, i.e., the observation light can be reflected by the separation mirror 50 and the measurement beam path 42 and the OCT beam path 130 can be transmitted by the separation mirror, or the latter two beam paths extend laterally past said mirror.

In a further exemplary embodiment, not illustrated, the patient's eye 12 can be ensured to be centered in relation to an optical appliance axis of the confocal system 40 for the purposes of increasing the reliability of the refraction measurement. In order to check the centration, the surgeon can gaze through the eyepieces 28 or use can be made of a camera image, said camera image having been recorded just before or during the refraction measurement by the camera 32 in the observation beam path. This image of the anterior chamber of eye can be used to ensure that the patient's eye 12 is correctly centered. The surgical microscope 10 according to an exemplary embodiment of the disclosure renders it possible to determine the location of the camera image at which the center the patient's pupil P must lie so that the chief ray of the measurement beam path 42 of the refraction measurement passes centrally through the patient's pupil. By way of example, after evaluating the camera image, the surgical microscope 10 could independently be moved into the position in which the pupil P of the patient's eye 12 is correctly positioned in a plane perpendicular to an optical axis of the main objective lens 20.

In summary, according to a first exemplary embodiment, an ophthalmic surgical microscope is provided including a main objective lens 20, through which an observation beam path 18 passes, and including a confocal optical system 40, which is designed as a refractometer for determining the refraction of an eye 12 of a patient, wherein the optical system 40 includes a measurement light source 52 for producing a measurement light beam 44, includes a measuring module 54 including a light detector 56 for measuring an intensity of measurement light and furthermore comprises an optical unit 60 through which the measurement beam path 42 passes in order to direct the measurement light beam 44 onto the retina 16 of the eye 12 and return measurement light 48 that has been reflected back at the retina 16 to the light detector 56, wherein the measurement beam path 42 is confocal overall, wherein the optical unit 60 includes an adaptive optical module (AOM), wherein a wavefront of the measurement beam path 42 can be modified by adjusting the adaptive optical module (AOM) such that the intensity of the back-reflected measurement light 48 measured by the light detector 56 changes, wherein the measuring module 54 is designed to ascertain the spherical equivalent (SE) of the ametropia of the eye 12 on the basis of a setting of the adaptive optical module (AOM), at which the measured intensity of the back-reflected measurement light 48 has a maximum, wherein the adaptive optical module (AOM) includes an adaptive component 74 that is designed to compensate an astigmatism in the wavefront of the measurement light beam path 42 by adjusting the adaptive component 74 and wherein the measuring module 54 is designed to ascertain the astigmatism C of the eye and the axis position φ of the astigmatism from a setting of the adaptive component 74 at which the measured intensity of the back-reflected measurement light 48 has a maximum.

According to a second exemplary embodiment, the adaptive component 74 is adjustable into a neutral setting, in which the adaptive component 74 has no astigmatic power or virtually no astigmatic power.

According to a third exemplary embodiment, the adaptive component 74 includes two cylindrical lenses that are twistable in relation to one another, the one cylindrical lens of which has a positive refractive power and the other cylindrical lens has a negative refractive power, wherein the positive and the negative refractive power are equal in terms of absolute value.

According to a fourth exemplary embodiment, the adaptive component 74 includes two plates which each have a surface contour, wherein the two surface contours are complementary to one another and wherein the plates are displaceable in translational fashion and/or twistable, together and/or relative to one another.

According to a fifth exemplary embodiment, the adaptive component 74 provides both an adjustable spherical refractive power for compensating the spherical equivalent of the ametropia and an adjustable astigmatic refractive power for compensating the astigmatism.

According to a sixth exemplary embodiment, the adaptive component 74 is positioned in a plane that is conjugate to a plane of a pupil (P) of the eye 12 during use of the surgical microscope 10.

According to a seventh exemplary embodiment, the measurement light source 52 and the light detector 56 are connected to an optical fiber 68, the free end 70 of which forms an emergence end for the measurement light beam 44 and an entrance end for the back-reflected measurement light 48, wherein the emergence end and the entrance end are confocal.

According to an eighth exemplary embodiment, a collimator 82 and 150, which is zoomable, is arranged in the measurement beam path 42.

According to a ninth exemplary embodiment, a lock-in amplifier is arranged in a measurement beam path 42, said lock-in amplifier including a chopper wheel 100.

According to a tenth exemplary embodiment, a deflection element 126 and 128 is arranged in the measurement beam path 42, said deflection element periodically deflecting the measurement light beam 44 in such a way that the measurement light being 44 is periodically moved on the retina 16 of the eye 12 during use of the surgical microscope 10.

According to an eleventh exemplary embodiment, the adaptive optical module (AOM) includes an afocal telescope 76 that is adjustable for compensating the spherical equivalent of the ametropia of the eye 12.

According to a twelfth exemplary embodiment, the optical unit 60 includes a first optical arrangement 80, through which the measurement beam path 42 passes, wherein the adaptive component 74 is arranged in the vicinity of a measurement light source-side focal plane of the first optical arrangement.

According to a thirteenth exemplary embodiment, as seen from the measurement light source 52, a second optical arrangement 81 which converts the measurement beam path 42 into a parallel beam path is disposed downstream of the first optical arrangement 80.

According to a fourteenth exemplary embodiment, a separation mirror 50 for separating observation beam path 18 and measurement beam path 42 is provided.

According to a fifteenth exemplary embodiment, the separation mirror 50 is arranged upstream of the main objective lens 20 as seen from the measurement light source 52 and the measurement beam path 42 passes through the main objective lens 20.

According to a sixteenth exemplary embodiment, the measurement beam path 42 passes through the main objective lens 20 in off-centered fashion in relation to an optical axis OA of the main objective lens 20.

According to a seventeenth exemplary embodiment, an illumination beam path for illuminating an observation area is provided, wherein the illumination beam path passes through part of the optical unit 60 of the optical system 40.

According to an eighteenth exemplary embodiment, the optical system 40/120 is additionally designed as an OCT system 120 for examining the eye 12 by optical coherence tomography.

According to a nineteenth exemplary embodiment, an OCT light source is formed by the measurement light source 52 for the refraction measurement and/or wherein an OCT detector is formed by the light detector 56 for the refraction measurement.

According to an twentieth exemplary embodiment, an OCT beam path 130 for recording an OCT scan passes through the same optical elements of the optical unit 60 as the measurement beam path 42 for the refraction measurement.

According to a twenty-first exemplary embodiment, the measurement beam path 42 for the refraction measurement passes through the same optical elements as an OCT beam path 130 for recording an OCT scan.

According to a twenty-second exemplary embodiment, an optical element 12 is present, said optical element, for the purposes of switching between a refraction measurement and recording of an OCT scan, being introducible into the measurement beam path 42 of the refraction measurement or into the OCT beam path 130 for recording an OCT scan or being removable from the measurement beam path 42 of the refraction measurement or from the OCT beam path 130 for recording an OCT scan.

According to a twenty-third exemplary embodiment, the optical unit 60 of the optical system 40/120 includes a scanning mirror arrangement 124 including two scanning mirrors 126 and 128.

According to a twenty-fourth exemplary embodiment, the at least one introducible or removable lens 132 is arranged in the OCT beam path during an OCT measurement in such a way that its focal plane is situated in the vicinity of the scanning mirror arrangement 124, typically between the two scanning mirrors 126 and 128, such that the adaptive component 74 is imaged into the plane of the pupil P of the eye 12 when recording an OCT scan.

According to a twenty-fifth exemplary embodiment, the at least one introducible or removable lens 132 is removed from the measurement beam path of the refraction measurement during a refraction measurement and wherein the adaptive component 74 is imaged into the plane of the pupil P of the eye 12 during a refraction measurement.

According to a twenty-sixth exemplary embodiment, the optical system includes a control unit 72 for adjusting the AOM.

According to a twenty-seventh exemplary embodiment, the control unit 72, more particularly in conjunction with the measuring module 54, is configured to adjust the AOM in such a way that the intensity of the back-reflected measurement light 48, as measured at the light detector 56, has a maximum.

According to a twenty-eighth exemplary embodiment, the control unit 72 is configured to initially adjust the AOM during a neutral setting of the adaptive component 74, in which the adaptive component 74 has no, or virtually no, astigmatic power, until the intensity measured at the light detector 56 has a maximum.

According to a twenty-ninth exemplary embodiment, the measuring module 54 is configured to at least approximately ascertain the spherical equivalent SE and the astigmatism C from the respective setting of the AOM when a first and a second maximum is detected at the light detector 56.

According to a thirtieth exemplary embodiment, the measuring module 54 is configured to ascertain the spherical equivalent SE and determine the astigmatism C as at least approximately zero from the setting of the AOM when only one maximum of the intensity is detected at the light detector 56.

According to a thirty-first exemplary embodiment, the control unit 72 is configured to set the adaptive component 74 in such a way that the adaptive component 74 compensates the astigmatism without consideration of the axis position thereof and configured to further adjust the adaptive component 74 until the intensity detected at the light detector 56 increases no more, wherein the measuring module 54 is configured to ascertain the axis position y of the astigmatism from the resultant setting of the adaptive component 74.

It is understood that the foregoing description is that of the exemplary embodiments of the disclosure and that various changes and modifications may be made thereto without departing from the spirit and scope of the disclosure as defined in the appended claims.

What is claimed is:
1. An ophthalmic surgical microscope, comprising:
a main objective lens through which an observation beam path passes;
a confocal optical system configured as a refractometer to determine a refraction of an eye of a patient and including:
a measurement light source to generate a measurement light beam;
a measuring module including a light detector to measure an intensity of measurement light; and
an optical unit through which a measurement beam path passes to direct the measurement light beam onto a retina of the eye of the patient and to return back-reflected measurement light reflected back at the retina to the light detector, the measurement beam path being confocal over an entire range of the measurement beam path, the optical unit including an adaptive optical module (AOM), a wavefront of the measurement beam path being modifiable by adjusting the AOM such that an intensity of the back-reflected measurement light measured by the light detector changes;
the measuring module being configured to determine a spherical equivalent of an ametropia of the eye based on a setting of the AOM, at which the intensity of the back-reflected measurement light measured by the light detector has a maximum;
the AOM including an adaptive component configured to compensate an astigmatism in the wavefront of the measurement beam path by adjusting the adaptive component; and
the measuring module being configured to determine the astigmatism of the eye and an axis position of the astigmatism from a setting of the adaptive component at which the measured intensity of the back-reflected measurement light has the maximum.

2. The ophthalmic surgical microscope as claimed in claim 1, wherein the adaptive component is adjustable to a neutral setting, in which the adaptive component has no astigmatic power or substantially no astigmatic power.

3. The ophthalmic surgical microscope as claimed in claim 1, wherein:
the adaptive component includes two cylindrical lenses twistable relative to one another,
a first cylindrical lens of the two cylindrical lenses has a positive refractive power and a second cylindrical lens of the two cylindrical lenses has a negative refractive power,
the positive and the negative refractive powers are equal in terms of an absolute value.

4. The ophthalmic surgical microscope as claimed in claim 1, wherein:
the adaptive component includes a first plate and a second plate,
the first plate has a first surface contour and the second plate has a second surface contour,
the first and second surface contours are complementary to one another, and
the first and second plates are displaceable in a translational fashion, twistable together, and/or twistable relative to one another.

5. The ophthalmic surgical microscope as claimed in claim 1, wherein the adaptive component provides an adjustable spherical refractive power to compensate the spherical equivalent of the ametropia, and an adjustable astigmatic refractive power to compensate the astigmatism.

6. The ophthalmic surgical microscope as claimed in claim 1, wherein the adaptive component is positioned in a plane that is conjugate to the plane of a pupil of the eye when the ophthalmic surgical microscope is being operated.

7. The ophthalmic surgical microscope as claimed in claim 1, further comprising:
an optical fiber having a free end, the free end forming an emergence end for the measurement light beam and an entrance end for the back-reflected measurement light,
wherein the measurement light source and the light detector are connected to the optical fiber, and
wherein the emergence end and the entrance end are confocal.

8. The ophthalmic surgical microscope as claimed in claim 1, further comprising:
a collimator arranged in the measurement beam path and being zoomable;
a lock-in amplifier arranged in the measurement beam path and including a chopper wheel; and
a deflection element arranged in the measurement beam path and periodically deflecting the measurement light beam to permit measurement light to be periodically moved on the retina of the eye when the ophthalmic surgical microscope is being operated.

9. The ophthalmic surgical microscope as claimed in claim 1, wherein:
the AOM includes an afocal telescope which is adjustable to compensate the spherical equivalent of the ametropia of the eye,
the confocal optical system includes a control unit to adjust the AOM,
the control unit is configured to:
initially adjust the AOM during a neutral setting of the adaptive component, in which the adaptive component has no, or virtually no, astigmatic power, until the intensity measured at the light detector has the maximum, and
adjust the AOM such that the intensity of the back-reflected measurement light, as measured at the light detector, has the maximum.

10. The ophthalmic surgical microscope as claimed in claim 9, wherein:
the optical unit includes a first optical arrangement, through which the measurement beam path passes and a second optical arrangement provided downstream of the first optical arrangement as seen from the measurement light source,
the adaptive component is arranged close to a measurement light source-side focal plane of the first optical arrangement, and.
the second optical arrangement converts the measurement beam path into a parallel beam path.

11. The ophthalmic surgical microscope as claimed in claim 1, further comprising:
a separation mirror to separate the observation beam path from the measurement beam path, and
wherein the separation mirror is arranged upstream of the main objective lens as seen from the measurement light source and the measurement beam path passes through the main objective lens.

12. The ophthalmic surgical microscope as claimed in claim 11, wherein the measurement beam path passes through the main objective lens in an off-centered fashion relative to an optical axis of the main objective lens.

13. The ophthalmic surgical microscope as claimed in claim 1, further comprising:
an illumination beam path to illuminate an observation area, and
wherein the illumination beam path passes through a part of the optical unit of the confocal optical system.

14. The ophthalmic surgical microscope as claimed in claim 1, wherein the confocal optical system is additionally configured as an optical coherence tomography (OTC) system to examine the eye by optical coherence tomography.

15. The ophthalmic surgical microscope as claimed in claim 14, wherein:
the measurement light source is an OCT light source to perform a refraction measurement,
the light detector acts as an OCT detector,
an OCT beam path passes through optical elements of the optical unit to record an OCT scan, and
the measurement beam path passes through the optical elements to perform the refraction measurement through which the OCT beam path passes to record the OCT scan.

16. The ophthalmic surgical microscope as claimed in claim 15, further comprising:
an optical element to switch between the refraction measurement and the recording of the OCT scan, wherein:
the optical element is arranged in the measurement beam path of the refraction measurement or into the OCT beam path to record the OCT scan, or
the optical element is removed from the measurement beam path of the refraction measurement or from the OCT beam path to record the OCT scan.

17. The ophthalmic surgical microscope as claimed in claim 15, wherein:
the optical unit of the confocal optical system includes a scanning mirror arrangement including two scanning mirrors, and
at least one lens is arranged in the OCT beam path during an OCT measurement such that a focal plane of the at least one lens is located between the two scanning mirrors, and the adaptive component is imaged into a plane of a pupil of the eye when the OCT scan is recorded.

18. The ophthalmic surgical microscope as claimed in claim 17, wherein:
the at least one lens is removed from the measurement beam path during the refraction measurement, and
the adaptive component is imaged into the plane of the pupil of the eye during the refraction measurement.

19. The ophthalmic surgical microscope as claimed in claim 9, wherein the measuring module is configured to:
at least approximately determine the spherical equivalent and the astigmatism from a setting of the AOM when a first maximum and a second maximum are detected at the light detector, and
determine the spherical equivalent and the astigmatism as being at least approximately zero from the setting of the AOM when only one maximum of the intensity is detected at the light detector.

20. The ophthalmic surgical microscope as claimed in claim 9, wherein:
the control unit is configured to:
set the adaptive component such that the adaptive component compensates the astigmatism without considering the axis position of the astigmatism,
further adjust the adaptive component until the intensity detected at the light detector increases no more, and the measuring module is configured to determine the axis position of the astigmatism from a resultant setting of the adaptive component.

* * * * *

UNITED STATES PATENT AND TRADEMARK OFFICE
CERTIFICATE OF CORRECTION

| | |
|---|---|
| PATENT NO. | : 11,147,447 B2 |
| APPLICATION NO. | : 16/526971 |
| DATED | : October 19, 2021 |
| INVENTOR(S) | : Markus Seesselberg et al. |

It is certified that error appears in the above-identified patent and that said Letters Patent is hereby corrected as shown below:

On the Title Page

For Item (56) FOREIGN PATENT DOCUMENTS,
Page 2: replace "JP 07023908 1/1999" with "JP 07023908 1/1995"

In the Specification

For BRIEF DESCRIPTION OF THE DRAWINGS, Column 13,
Line 48: replace "FIG. 16B shows a magnified section of FIG. 16B;" with "FIG. 16B shows a magnified section of FIG. 16A;"

For DESCRIPTION OF EXEMPLARY EMBODIMENTS, Column 20,
Line 50: replace "SC" with "SE"

For Column 29,
Line 51: replace "Shown" with "shown"

For Column 30,
Line 58: replace "of eye" with "of the eye"

For Column 33,
Line 60: replace "axis position y" with "axis position φ"

In the Claims

For Claim 3, Column 34,
Line 49: add " and" after "power,"

For Claim 14, Column 36,
Line 9: replace "(OTC)" with "(OCT)"

Signed and Sealed this
First Day of November, 2022

Katherine Kelly Vidal
*Director of the United States Patent and Trademark Office*